United States Patent
Paton et al.

(10) Patent No.: US 7,078,489 B2
(45) Date of Patent: Jul. 18, 2006

(54) CYTOTOXIN WITH A SUBTILASE DOMAIN

(75) Inventors: Adrienne Webster Paton, Parkside (AU); James Cleland Paton, Parkside (AU)

(73) Assignee: Adelaide Research & Innovation Pty, Ltd. (AU)

( * ) Notice: Subject to any disclaimer, the term of this patent is extended or adjusted under 35 U.S.C. 154(b) by 141 days.

(21) Appl. No.: 10/844,096

(22) Filed: May 12, 2004

(65) Prior Publication Data

US 2005/0136424 A1 Jun. 23, 2005

(30) Foreign Application Priority Data

Dec. 22, 2003 (AU) .............................. 2003907058

(51) Int. Cl.
*C07K 14/00* (2006.01)
(52) U.S. Cl. ..................................................... 530/350
(58) Field of Classification Search ................. 530/350
See application file for complete search history.

(56) References Cited

OTHER PUBLICATIONS

Patton et al. 2001; Characterization of Saa, a Novel Autoagglutinating Adhesion Produced by Locus of Enterocyte Effacement-Negative Shiga-Toxigenic *Escherichia coli* Strains That Are Virulent for Humans. Infection and Immunity 69(11): 6999-7009.*

Srimanote et al. 2002; Characterization of a Novel Type IV Pilus Locus Encoded on the Larg Plasmid of Locus of Enterocyte Effacement-Negative Shiga-Toxigenic *Escherichia coli* Strains That Are Virulent for Humans. Infection and Immunity, 70(6): 3094-3100.*

Paton et al. 2004; A New Family of Potent AB5 Cytotoxins Produced by Shiga Toxigenic *Escherichia coli*. J. Exp. Med. 200(1): 35-46.*

* cited by examiner

*Primary Examiner*—Karen Cochrane Carlson
(74) *Attorney, Agent, or Firm*—Henry D. Coleman; R. Neil Sudol; William J. Sapone

(57) ABSTRACT

A member of a new class of bacterial toxin has been isolated and characterised. The bacterial toxin is of the $AB_5$ type and is characterised in that it has a subtilase domain. It is cytotoxic to Vero cells, and toxicity in vivo in mice occurs in a number of different sites. Mutation of the serine active residue results in greater than 99% reduction in activity. The protein has been purified and antibodies have been prepared for both the A subunit and B subunits, and ELISA detection methods have been developed. The nucleic acid sequence has been determined and primers specific for the toxin have been used for a preliminary screen of a range of patient samples to ascertain the extent to which the toxin is present.

19 Claims, 8 Drawing Sheets

|  | Asp catalytic domain | His catalytic domain | Ser catalytic domain |
|---|---|---|---|
| SubA | 48          59<br>VSVVDSGVAFIG<br>     \* | 89        99<br>HGTAMASLIAS<br> \* | 269     279<br>GTSEATAIVSG<br>  \* |
| Consensus subtilase | SxLLDDGLxxxD<br>T  II S  I     N<br>A  VV T  V     H<br>I  MM A  M<br>V  F     F<br>          C | HGSxVSGxLSS<br>T  ITS ITA<br>M  CA  VAG<br>    G   MGM<br>    C   AC<br>         L<br>         V | GTSxSxPxxSA<br>   A       TG<br>            A<br>            V<br>            C |

DNA and deduced a.a. sequence of subAB region of pO113.

__US 7,078,489 B2__

SEQUENCE LISTING

```
<160> NUMBER OF SEQ ID NOS: 25

<210> SEQ ID NO 1
<211> LENGTH: 1740
<212> TYPE: DNA
<213> ORGANISM: Escherichia coli
<220> FEATURE:
<223> OTHER INFORMATION: subA subB genes

<400> SEQUENCE: 1
gctttccaac cgtgttgacg aactgctgcc atggaaagta gttttcaccg ataaataaga     60
gtcaatacgg cgctctgttg acgcttacat ttgtaactaa ctggaggagc ttatgcttaa    120
gattttatgg acgtatattc tattcctgct ttttatatct gcgtcagcta gggcggaaaa    180
accctggtat tttgatgcaa ttggtctgac agaaacaaca atgtctctta cagacaaaaa    240
taccccagtg gtcgtatctg ttgttgattc cggagtggca tttattggag gtctcagcga    300
tagtgaattt gcaaaattta gttttactca ggatggttca ccgttcccgg taaaaaagtc    360
tgaagcttta tatattcatg gtactgctat ggcttccctc attgcctcac gttatgggat    420
```

```
ttatggtgtt tatcctcatg ctctgatatc cagtagaaga gttattcctg acggtgtaca    480
ggactcatgg attagagcaa ttgaaagcat tatgtcgaat gttttcttg ctccaggaga     540
agagaaaatc attaatatat cgggaggcca aagggagtg gcttccgcat cggtctggac     600
agaactgctt tcccgtatgg gcagaaataa tgatcgatta attgttgcgg cagtgggtaa    660
tgatggcgct gatatacgca aactgagtgc tcagcagaga atatggccag cggcttatca    720
tcctgtcagc agtgtgaata aaagcaaga tcctgtgata agagtcgctg ccctggcaca    780
gtaccggaaa ggagaaacac cggtattgca tggtggagga attaccggaa gtcggttcgg   840
gaacaattgg gttgatattg ctgcaccagg gcagaatatt acattcctca gacctgatgc    900
caaaacgggg actggtagcg gaacgtcaga agcaacagct atagtttccg gcgtactggc    960
agcaatgacc tcatgtaatc cccgggcaac agcgacagaa ctgaagcgaa cgctgctgga   1020
gtctgcagat aaatacccct cacttgtaga taaagtgaca gaagggaggg ttttgaatgc   1080
agaaaaagcg attagtatgt tttgcaagaa aaattatat cctgtccgtc agggaaggat    1140
gagtgaagaa ctgtaaaata ccggaggtgc atatgacgat taagcgtttt tttgtgtgtg   1200
caggtattat gggatgtcta tcccttaatc cagctatggc tgagtggact ggtgatgccc   1260
gggatggcat gttttcaggc gttgttatta cccagtttca tacaggacaa atagacaata   1320
aaccttattt ttgtattgag gggaaacaat cggcaggctc ctccataagt gcctgctcga   1380
tgaagaattc gtcagtctgg ggggcttcgt tttccacatt atacaatcaa gcattatatt   1440
tttacacaac aggccagccg gtcaggattt attataaacc cggagtatgg acgtatccac   1500
cttttgtgaa ggcattaacg tccaatgctc ttgttgggtt atcaacctgc accacatcga   1560
cagaatgttt tggtcctgac aggaaaaaga actcataagt gataatcgtc ttatatcact   1620
ggcgctgact cgctgatctg tcccgatcat ggcacatata ttccgccaat gctgtatgct   1680
ggtataccac tgaaggtcca gcatagtctg gtagggcata agtctatcag cttaatgggg   1740
```

<210> SEQ ID NO 2
<211> LENGTH: 347
<212> TYPE: PRT
<213> ORGANISM: Escherichia coli
<220> FEATURE:
<223> OTHER INFORMATION: subA

<400> SEQUENCE: 2

Met Leu Lys Ile Leu Trp Thr Tyr Ile Leu Phe Leu Leu Phe Ile
1               5                   10                  15

Ser Ala Ser Ala Arg Ala Glu Lys Pro Trp Tyr Phe Asp Ala Ile
                20                  25                  30

Gly Leu Thr Glu Thr Thr Met Ser Leu Thr Asp Lys Asn Thr Pro
            35                  40                  45

Val Val Val Ser Val Val Asp Ser Gly Val Ala Phe Ile Gly Gly
        50                  55                  60

Leu Ser Asp Ser Glu Phe Ala Lys Phe Ser Phe Thr Gln Asp Gly
    65                  70                  75

Ser Pro Phe Pro Val Lys Lys Ser Glu Ala Leu Tyr Ile His Gly
            80                  85                  90

Thr Ala Met Ala Ser Leu Ile Ala Ser Arg Tyr Gly Ile Tyr Gly
        95                  100                 105

Val Tyr Pro His Ala Leu Ile Ser Ser Arg Arg Val Ile Pro Asp
            110                 115                 120

Gly Val Gln Asp Ser Trp Ile Arg Ala Ile Glu Ser Ile Met Ser

```
                    125                 130                 135
Asn Val Phe Leu Ala Pro Gly Glu Glu Lys Ile Ile Asn Ile Ser
                140                 145                 150
Gly Gly Gln Lys Gly Val Ala Ser Ala Ser Val Trp Thr Glu Leu
                155                 160                 165
Leu Ser Arg Met Gly Arg Asn Asn Asp Arg Leu Ile Val Ala Ala
                170                 175                 180
Val Gly Asn Asp Gly Ala Asp Ile Arg Lys Leu Ser Ala Gln Gln
                185                 190                 195
Arg Ile Trp Pro Ala Ala Tyr His Pro Val Ser Ser Val Asn Lys
                200                 205                 210
Lys Gln Asp Pro Val Ile Arg Val Ala Ala Leu Ala Gln Tyr Arg
                215                 220                 225
Lys Gly Glu Thr Pro Val Leu His Gly Gly Ile Thr Gly Ser
                230                 235                 240
Arg Phe Gly Asn Asn Trp Val Asp Ile Ala Ala Pro Gly Gln Asn
                245                 250                 255
Ile Thr Phe Leu Arg Pro Asp Ala Lys Thr Gly Thr Gly Ser Gly
                260                 265                 270
Thr Ser Glu Ala Thr Ala Ile Val Ser Gly Val Leu Ala Ala Met
                275                 280                 285
Thr Ser Cys Asn Pro Arg Ala Thr Ala Thr Glu Leu Lys Arg Thr
                290                 295                 300
Leu Leu Glu Ser Ala Asp Lys Tyr Pro Ser Leu Val Asp Lys Val
                305                 310                 315
Thr Glu Gly Arg Val Leu Asn Ala Glu Lys Ala Ile Ser Met Phe
                320                 325                 330
Cys Lys Lys Asn Tyr Ile Pro Val Arg Gln Gly Arg Met Ser Glu
                335                 340                 345
Glu Leu

<210> SEQ ID NO 3
<211> LENGTH: 152
<212> TYPE: PRT
<213> ORGANISM: Rhodococcus equii
<220> FEATURE:
<223> OTHER INFORMATION: sequence containing antigenic determinant of
      VapA

<400> SEQUENCE: 3

Met Thr Ile Lys Arg Phe Phe Val Cys Ala Gly Ile Met Gly Cys
  1               5                  10                  15
Leu Ser Leu Asn Pro Ala Met Ala Glu Trp Thr Gly Asp Ala Arg
                 20                  25                  30
Asp Gly Met Phe Ser Gly Val Val Ile Thr Gln Phe His Thr Gly
                 35                  40                  45
Gln Ile Asp Asn Lys Pro Tyr Phe Cys Ile Glu Gly Lys Gln Ser
                 50                  55                  60
Ala Gly Ser Ser Ile Ser Ala Cys Ser Met Lys Asn Ser Ser Val
                 65                  70                  75
Trp Gly Ala Ser Phe Ser Thr Leu Tyr Asn Gln Ala Leu Tyr Phe
                 80                  85                  90
Tyr Thr Thr Gly Gln Pro Val Arg Ile Tyr Tyr Lys Pro Gly Val
                 95                 100                 105
Trp Thr Tyr Pro Pro Phe Val Lys Ala Leu Thr Ser Asn Ala Leu
```

-continued

```
                    110                 115                 120
Val Gly Leu Ser Thr Cys Thr Thr Ser Thr Glu Cys Phe Gly Pro
                125                 130                 135
Asp Arg Lys Lys Asn Ser Asn Leu Gln Lys Asp Glu Pro Asn Gly
                140                 145                 150
Arg Ala

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
gtacggacta acagggaact g                                            21

<210> SEQ ID NO 5
<211> LENGTH: 19
<212> TYPE: DNA
<213> ORGANISM: Artificial Sequence
<220> FEATURE:
<223> OTHER INFORMATION: Primer

<400> SEQUENCE: 5
atcgtcatat gcacctccg                                               19

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
gtagataaag tgacagaagg g                                            21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gcaaaagcct tcgtgtagtc                                              20

<210> SEQ ID NO 8
<211> LENGTH: 31
<212> TYPE: DNA
<213> ORGANISM: Artificial Sequence
<220> FEATURE:
<223> OTHER INFORMATION: Primer

<400> SEQUENCE: 8
ggtagcggaa cggcagaagc aacagctata g                                 31

<210> SEQ ID NO 9
<211> LENGTH: 32
<212> TYPE: DNA
<213> ORGANISM: Artificial Sequence
<220> FEATURE:
<223> OTHER INFORMATION: Primer

<400> SEQUENCE: 9
```
agctgttgct tctgccgttc cgctaccagt cc    32

<210> SEQ ID NO 10
<211> LENGTH: 60
<212> TYPE: DNA
<213> ORGANISM: Artificial Sequence
<220> FEATURE:
<223> OTHER INFORMATION: Primer

<400> SEQUENCE: 10 tacccagtg gtcgtatctg ttgttgattc cggagtggca gtgtaggctg gagctgcttc    60

<210> SEQ ID NO 11
<211> LENGTH: 60
<212> TYPE: DNA
<213> ORGANISM: Artificial Sequence
<220> FEATURE:
<223> OTHER INFORMATION: Primer

<400> SEQUENCE: 11
tgtcacttta tctacaagtg aagggtattt atctgcagac catatgaata tcctccttag    60

<210> SEQ ID NO 12
<211> LENGTH: 60
<212> TYPE: DNA
<213> ORGANISM: Artificial Sequence
<220> FEATURE:
<223> OTHER INFORMATION: Primer

<400> SEQUENCE: 12
tgtctatccc ttaatccagc tatggctgag tggactggtg gtgtaggctg gagctgcttc    60

<210> SEQ ID NO 13
<211> LENGTH: 61
<212> TYPE: DNA
<213> ORGANISM: Artificial Sequence
<220> FEATURE:
<223> OTHER INFORMATION: Primer

<400> SEQUENCE: 13
attctgtcga tgtggtgcag gttgataacc caacaagagc acatatgaat atcctcctta    60
g    61

<210> SEQ ID NO 14
<211> LENGTH: 31
<212> TYPE: DNA
<213> ORGANISM: Artificial Sequence
<220> FEATURE:
<223> OTHER INFORMATION: Primer

<400> SEQUENCE: 14
ccctggggat ccgatgcaat tggtctgaca g    31

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
gttcgagctc actcatcctt ccctgacg    28

<210> SEQ ID NO 16

```
<211> LENGTH: 30
<212> TYPE: DNA
<213> ORGANISM: Artificial Sequence
<220> FEATURE:
<223> OTHER INFORMATION: Primer

<400> SEQUENCE: 16
ggtggcatgc gggggatggc atgttttcag                                        30

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
cttagagctc cttttcctg tcaggacc                                           28

<210> SEQ ID NO 18
<211> LENGTH: 31
<212> TYPE: DNA
<213> ORGANISM: Artificial Sequence
<220> FEATURE:
<223> OTHER INFORMATION: Primer

<400> SEQUENCE: 18
ttgtaaggat ccggaggagc ttatgcttaa g                                      31

<210> SEQ ID NO 19
<211> LENGTH: 33
<212> TYPE: DNA
<213> ORGANISM: Artificial Sequence
<220> FEATURE:
<223> OTHER INFORMATION: Primer

<400> SEQUENCE: 19
gattatctcg agtgagttct ttttcctgtc agg                                    33

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
cgaatgtttt tcttgctcca g                                                 21

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
acactgctga caggatgata ag                                                22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
```

```
gttttcaggc gttgttatta cc                                                    22

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23 cacaaaggt ggatacgtcc                                                        20

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
gcagataaat acccttcact tg                                                    22

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
atcaccagtc cactcagcc                                                        19
```

CYTOTOXIN WITH A SUBTILASE DOMAIN

PRIORITY

This application claims foreign priority to Australian application 2003907058, filed Dec. 22, 2003.

FIELD OF THE INVENTION

This invention relates to an isolated cytotoxin with a subtilase domain, isolated subunits thereof, polynucleotides encoding the same, diagnostic probes and primers, antibodies thereto and fragments thereof, and modified proteins thereof.

BACKGROUND OF THE INVENTION $AB_5$ toxins produced by pathogenic bacteria comprise an A subunit with enzymic activity and a pentameric B subunit responsible for interaction with glycolipid receptors on target eukaryotic cells (1). The three $AB_5$ toxin families recognised to date are the Shiga toxins (Stx), Cholera toxin (Ctx) and the related *Escherichia coli* heat labile enterotoxins (LT), and pertussis toxin (Ptx). In each case, they are key virulence determinants of the bacteria that produce them (Shiga toxigenic *E. coli* [STEC] and *Shigella dysenteriae, Vibrio cholerae* and enterotoxigenic *E. coli* [ETEC], and *Bordetella pertussis*, respectively). Collectively, these pathogens cause massive global morbidity and mortality, accounting for millions of deaths each year, particularly amongst children in developing countries. The $AB_5$ toxins exert their catastrophic effects by entering their respective target cells (usually by receptor-mediated endocytosis), and then inhibiting or corrupting essential host functions. The A subunits of Stx toxins have RNA-N-glycosidase activity, and cleave 28S rRNA, thereby inhibiting host protein synthesis. The A subunits of Ctx/LT and Ptx are ADP-ribosylases which modify distinct host G proteins, resulting in alteration of intracellular cAMP levels and disregulation of ion transport mechanisms (1).

SUMMARY OF THE INVENTION

The inventors have isolated a novel toxin characterised in having a subtilase domain, which is shown to be essential for full toxin activity.

Therefore in a first aspect the invention might be said to reside in an isolated bacterial toxin comprising an A subunit and two or more B subunits, the A subunit having a subtilase domain, said toxin being cytotoxic to Vero cells.

In a second form the invention might be said to reside in an isolated nucleic acid encoding a bacterial toxin comprising an A subunit and two or more B subunits, the A subunit having a subtilase domain.

In a second aspect of the second form the invention might be said to reside in an isolated nucleic acid encoding an $AB_5$ bacterial toxin, or subunit or fragment thereof having a sequence selected from the group consisting of
   a) SEQ ID NO 1,
   b) a sequence at least 80% identical to the sequence of SEQ ID NO 1 or the complement of SEQ ID NO 1,
   c) a strand that hybridizes under high stringency conditions to a single probe, the sequence of which consists of SEQ ID NO 1 or the complement of SEQ ID NO:1, the A subunit of the toxin having a subtilase domain.

In another aspect of the second form the invention might be said to reside in an isolated nucleic acid encoding the A subunit or fragment thereof of an $AB_5$ bacterial toxin, said nucleic acid having a sequence selected from the group consisting of
   d) a sequence encoding amino acids of the sequence set forth in SEQ ID NO 2,
   e) a sequence encoding amino acid residues 22 to 347 of SEQ ID NO 2,
   f) a sequence encoding an amino acid sequence which is at least 70% identical to the sequence comprising amino acid residues 22 to 347 SEQ ID No 2,
   g) a sequence encoding a fragment of the A subunit comprising at least 50 amino acids of SEQ ID NO 2, the A subunit or fragment thereof having a subtilase domain.

In an alternate form of the second form the invention might be said to reside in an isolated nucleic acid encoding the B subunit or fragment thereof of an $AB_5$ bacterial toxin, said nucleic acid having a sequence selected from the group consisting of one
   h) a sequence encoding amino acid sequence as set forth in SEQ ID NO 3,
   i) a sequence encoding amino acid sequence of residues 24 to 141 of SEQ ID NO 3,
   j) a sequence encoding an amino acid sequence which is at least 70% identical to the sequence comprising amino acids 24 to 141 SEQ ID No 3,
   k) a sequence encoding a fragment of the B subunit comprising at least 50 amino acids, the A subunit having a subtilase domain.

The invention might take the form of a vector or a recombinant DNA construct having at least one regulatory sequence. Alternatively the invention might comprise an expression cassette comprising a polynucleotide sequence encoding the toxin, subunit or fragment of the invention placed under the control of elements required for expression of the polynucleotide sequence, or a host cell transformed by the nucleic acid of this invention.

In a third form the invention might be said to reside in a method of production of a bacterial toxin comprising the steps of cultivating cells carrying exogenous nucleic acid encoding the toxin, under conditions that allow for the synthesis of the toxin and isolating the toxin from the cultivated cells or from the culture medium or from both the cultivated cells and the culture medium.

In a fourth form the invention might be said to reside in an isolated bacterial $AB_5$ toxin, or subunits thereof, the A subunit having a subtilase domain, said toxin being cytotoxic to Vero cells.

In a second aspect of the fourth form the invention might be said to reside in an isolated A subunit or fragment thereof of an $AB_5$ bacterial toxin, said A subunit having an amino acid sequence selected from the group consisting of
   d) SEQ ID NO 2,
   e) residues 22 to 347 of SEQ ID NO 2,
   f) a sequence which is at least 70% identical to the sequence comprising amino acids 22 to 347 SEQ ID No 2,
   g) a fragment of the A subunit comprising at least 50 amino acids of SEQ ID NO 2, the A subunit or fragment thereof having a subtilase domain.

In a third aspect of the fourth form the invention might be said to reside in an isolated subunit B or fragment thereof of an AB$_5$ bacterial toxin, said subunit B having a sequence selected from the group consisting of one
h) SEQ ID NO 3,
i) residues 24 to 141 of SEQ ID NO 3,
j) a sequence which is at least 70% identical to the sequence comprising amino acids 24 to 141 SEQ ID No 3,
k) a fragment of the B subunit comprising at least 50 amino acids of SEQ ID NO 3, the A subunit of the toxin having a subtilase domain.

In a fifth form the invention might be said to reside in an antibody or antibody fragment directed against an AB$_5$ bacterial toxin, subunit or fragment thereof, said bacterial toxin or fragment having a subtilase domain.

In a sixth form the invention might be said to reside in a method of immunising a mammal to reduce the effects of a bacterial toxin having a subtilase domain, including the step of administering to the mammal a pharmaceutically acceptable preparation including a non-toxic mutant of the toxin.

In a seventh form the invention might be said to reside in a method amplifying the nucleic acid encoding the toxin of the invention in a sample containing the nucleic acid, including the sequential steps of suitable heat separation, contacting the sample with primer pairs specific for said nucleic acid in the presence of nucleotide polymerase and nucleotides necessary for polymerisation.

In an eighth form the invention might be said to reside in a method of detecting the presence of a nucleic acid encoding the toxin of this invention in a sample containing the nucleic acid including the step of contacting the sample with a nucleic acid probe, washing off non bound probe and detecting bound probe.

In a ninth form the invention might be said to reside in a method of detecting the presence of the toxin of the present invention in a sample, including the steps of contacting the sample with antibodies or fragments thereof directed against the toxin, wherein either the sample or the antibodies are bound to a solid phase support, washing away unbound material, and detecting the presence of either bound antibody or toxin.

BRIEF DESCRIPTION OF THE DRAWINGS

FIG. 1 Alignment of the three putative catalytic domains of SubA with the consensus sequence for Asp, His and Ser catalytic domains of members of the subtilase family (7). The numbers above the SubA fragments indicate residue number of the terminal amino acids. Alternative consensus residues at a given position are shown vertically. The known active site residues in each subtilase catalytic domain (7) are shown in bold type and underlined. * denotes SubA residues that do not match the consensus sequence.

FIG. 8 Serum anti-SubAB levels in mice challenged with SubAB-producing clones. Sera were collected from mice on day 15 after challenge with E. coli DH5α$^{SR}$ carrying pK184 (solid circles), pK184subAB (solid squares), or pK184subA$_{A271}$B (solid triangles), and assayed for antibodies to SubAB by ELISA, as described in the Materials and Methods. The minimum detectable titer was 50, and sera below this have been assigned a nominal titer of 25.

FIG. 9 Nucleotide sequence showing the sequences of subunit A and subunit B genes (SEQ ID NO. 1). The location of respective ribosome binding sites are indicated by bolded text and by the letters RBS. The deduced amino acid sequence for both subunit A (SEQ ID NO. 2) and subunit B (SEQ ID NO. 3) are shown in single letter code. The deduced Ap, His and Ser subtilase catalytic motifs are indicated by shading. A putative termination loop is shown by two converging arrows underlining an end part of the sequence.

Figure 2:
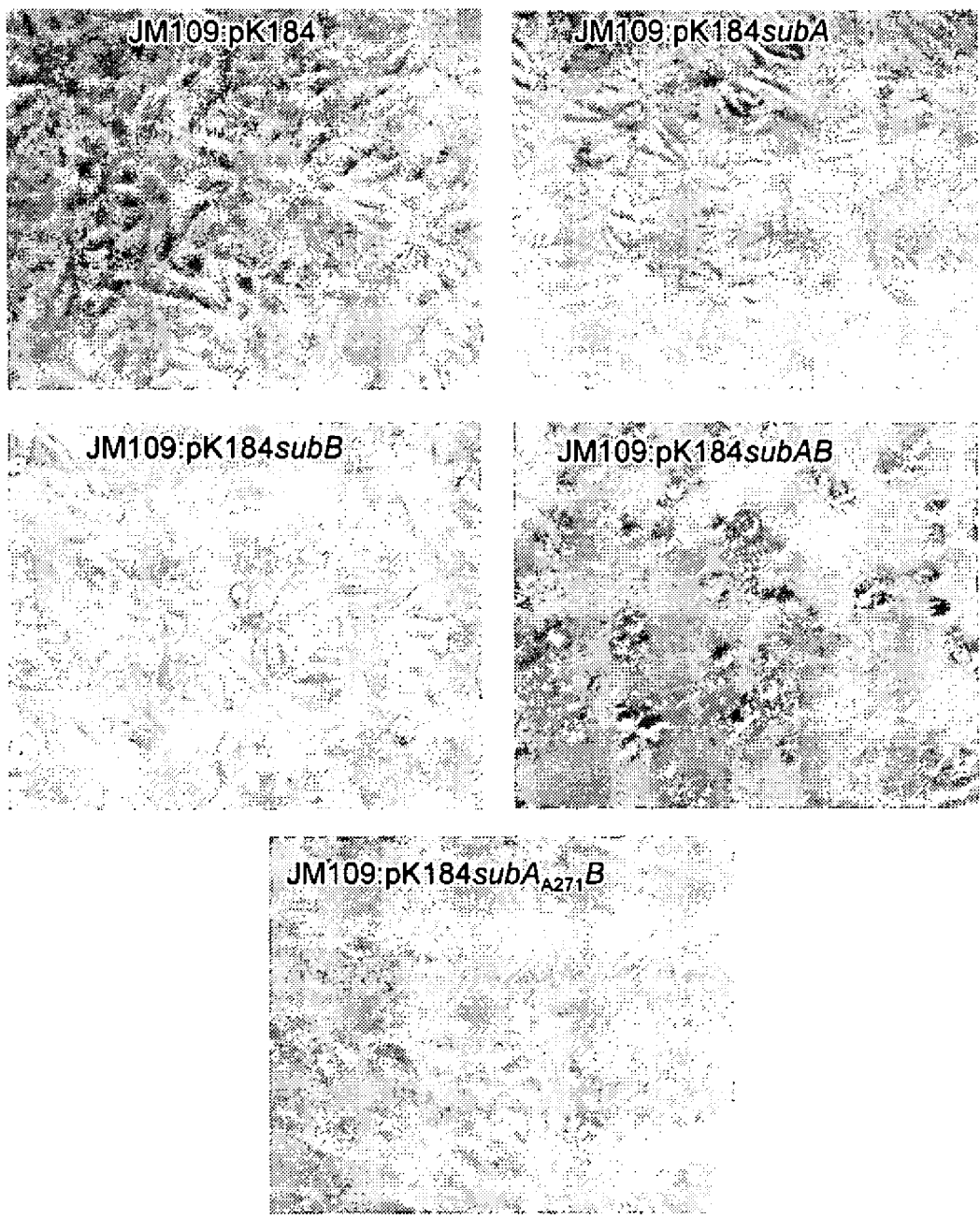
FIG. 2. Cytotoxicity of SubAB for Vero cells. Monolayers were treated with 1:80 dilutions of culture supernatant from the indicated strains for 72 h and photographed under phase-contrast microscopy.

DETAILED DESCRIPTION OF THE ILLUSTRATED AND EXEMPLIFIED EMBODIMENTS OF THE INVENTION

For the purpose of this specification the word "comprising" means "including but not limited to", and the word "comprise" has a corresponding meaning.

By way of a shorthand notation the following three and one letter abbreviations for amino acid residues are used in the specification as defined in Table 1.

Where a specific amino acid residue is referred to by its position in the polypeptide of an protein, the amino acid abbreviation is used with the residue number given in superscript (i.e. $Xaa_n$)

TABLE 1

| Amino Acid | Three-letter Abbreviation | One letter Abbreviation |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

In a first aspect the invention might be said to reside in an isolated bacterial toxin comprising an A subunit and two or more B subunits, the A subunit having a subtilase domain, said toxin being cytotoxic to Vero cells.

The precise configuration of A and B subunits has not yet been elucidated. It is expected that in line with other toxins carried by enteric bacteria (Shiga toxins (Stx), Cholera toxin (Ctx), *Escherichia coli* heat labile toxin (LT) and Pertussis toxin (Ptx)) that this will prove to be in an $AB_5$ configuration. However that is not to say that a different configuration may prove to be exhibited such as an $AB_4$ or other configuration.

The A subunit is estimated as having a molecular weight of about 35 kD.

Preferably the B subunit imparts specificity to cell surface recognition and preferably the specificity is determined by one or more sugars of the cell surface, and in one specific form the specificity imparted by the B subunit is to the oligosaccharide component of GM2 (GalNAcβ[1→4](NeuAcα[2→3])Galβ[1→4]Glcβ-).

The binding specificity need not necessarily be an exclusive binding specificity. Toxins might bind to more than one sugar moiety, however generally they bind with more avidity to one particular sugar moiety and this moiety is indicated as the specificity. Where more than one sugar moiety can be bound these tend to be related in structure.

Preferably the B subunit has an estimated molecular weight of about 13 kD.

The exemplified isolated cytotoxin has a very high cytotoxicity for Vero cells being as high or higher than other bacterial $AB_5$ toxins for the cell type to which they have specificity. Accordingly in one form the toxicity of the isolated cytotoxin may be greater than $10^9$ $CD_{50}$ per mg toxin and preferably is greater than $10^{10}$ $CD_{50}$ per mg toxin.

Whilst the first aspect of the invention contemplates the isolation of the toxin with two subunits presented in their assembled form, the second aspect of the invention contemplates isolation of the subunits separately. Thus in a first form of this second aspect the invention might relate to a separately purified subunit A of the cytotoxin and a second form of this second aspect the invention might relate to a separately purified subunit B of the cytotoxin.

Figure 9:
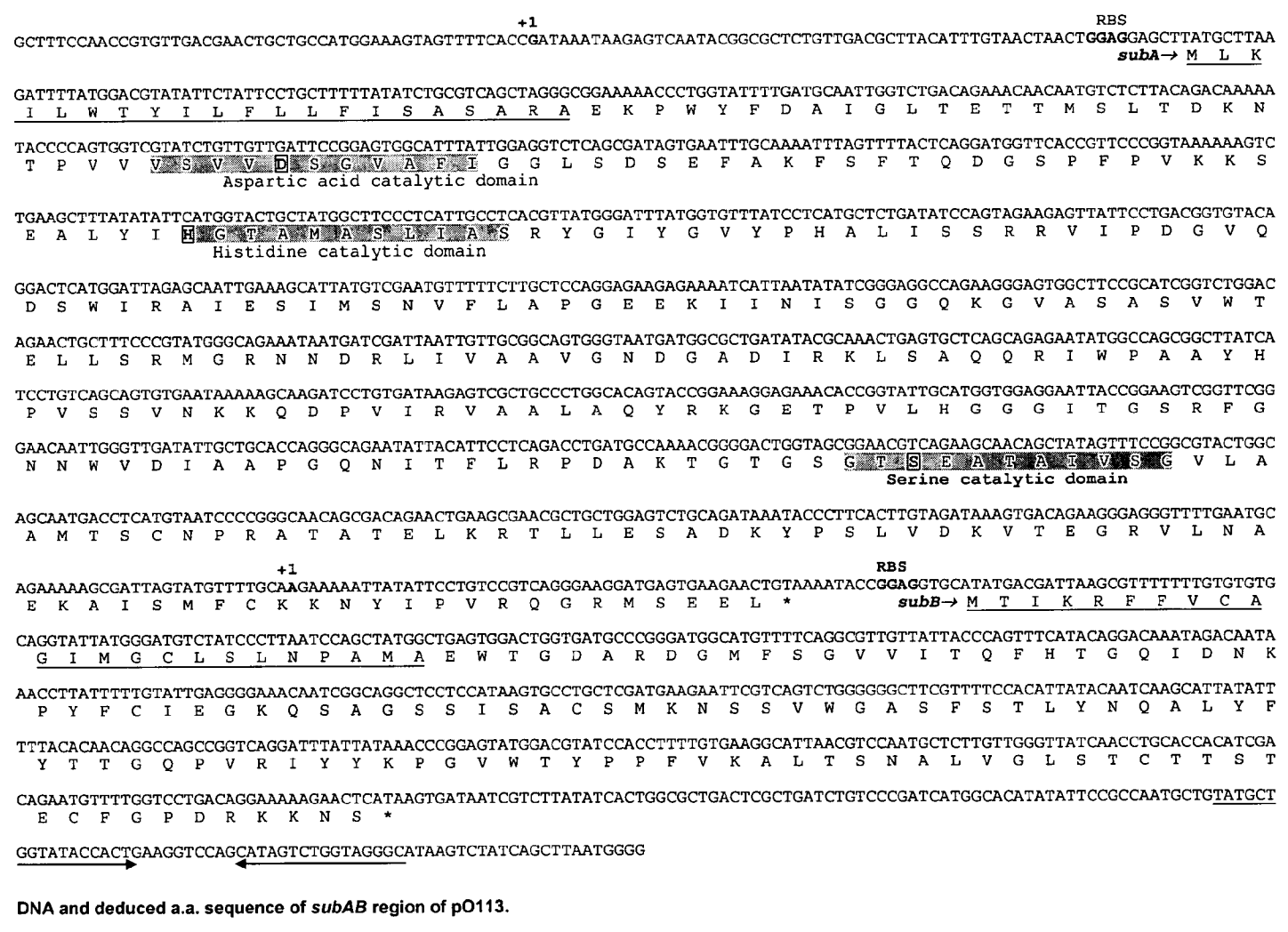

The predicted amino acid sequence of the subtilase toxin is set out in FIG. 9. In a very specific form the subunit A of the subtilase toxin is as set out in FIG. 9, and in another very specific form the subunit B of the subtilase toxin is as set out in FIG. 9.

A subunit with variations in the amino acids however may still have function with 70, 80, 90 or 95% similarity. Function may include all the functions of the wild type subunit or alternatively may selectively exclude one or other such function but retain the other functions being those perhaps of particular interest.

The invention contemplates variation comprising one or more amino acid residues within the sequence being substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Particularly conservative amino acid substitutions are:
(a) Lys for Arg or vice versa such that a positive charge may be maintained;
(b) Glu for Asp or vice versa such that a negative charge may be maintained;
(c) Ser for Thr or vice versa such that a free OH can be maintained;
(d) Gln for Asn or vice versa such that a free NH2 can be maintained;
(e) Ile for Leu or for Val or vice versa as roughly equivalent hydrophobic amino acids; and
(f) Phe for Tyr or vice versa as roughly equivalent aromatic amino acids.

However, it will be understood that less conservative substitutions may still be made without affecting the activity of the toxin.

The invention also encompasses chimeric proteins such as ones that may be useful for purification (e.g. with His6 tag). The isolated proteins may or may not include a signal sequence such is normally encoded therefore, alternatively it may include other sequences that assist in having the toxin exported.

Modifications may be made to improve various properties of the toxin or to facilitate the cloning, expression, and the like. Modifications to enhance cloning and expression are well known to those of skill in the art and include, for example, a methionine added at the amino terminus to provide an initiation site, or additional amino acids that form a purification tag (e.g., poly His) placed on either terminus to facilitate purification. In addition, one of skill will recognize that fusion proteins with various heterologous protein sequences can be prepared. For example, overexpression of a protein can lead to the accumulation of folding intermediates which have a tendency to aggregate. Production of fusion proteins including sequences, such as bacterial thioredoxin, can be used to facilitate proper folding. The polypeptides of the invention can also be fused to other proteins to allow quantification or localization of the linked protein. Thus, the fusion partner can be detected by the presence of the peroxidase activity of the enzyme of the invention. The fusion partner may also be a bacterial protein that results in increased yields, because normal prokaryotic control sequences direct transcription and translation. In *E. coli*, lacZ fusions are often used to express heterologous proteins. Suitable vectors are readily available, such as the pUR, pEX, and pMRI1000 series (see, e.g., Sambrook et al., supra.).

For certain applications, it may be desirable to cleave the non-toxin amino acids from the fusion protein after purification. This can be accomplished by any of several methods known in the art, including cleavage by cyanogen bromide, a protease (e.g., enterokinase), or by Factor $X_a$, (see, e.g., Sambrook et al., supra.; Itakura et al., Science (1977) 198: 1056; Goeddel et al., Proc. Natl. Acad. Sci. USA (1979) 76: 106; Nagai et al., Nature (1984) 309: 810; Sung et al., Proc. Natl. Acad. Sci. USA (1986) 83: 561). Cleavage sites can be engineered into the gene for the fusion protein at the desired point of cleavage.

A suitable system for obtaining recombinant proteins from *E. coli* which maintains the integrity of their N-termini has been described by Miller et al Biotechnology 7:698–704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal reside.

Additionally the invention encompasses altered proteins that may have reduced toxin or cell recognition activity.

In particular reduced toxin activity may be useful for eliciting a protective immune response. Sequences for the active site of the subtilase gene is set out in FIG. 1. It has been found that alteration of at least one key amino acid in one motif of the active site leads to inactivity (see below). Thus the alteration may encompass one or more amino acid substitutions in any one of the Asp, His or Ser catalytic domains to reduce the subtilase activity. Reduction of activity is preferably at least 50, 60, 70, 80, 90, 95 or 99%.

Amino acid substitutions are other than set out in FIG. 1 as suitable alternatives, and do not include substitutions set out as "x" in the positions so marked.

Preferably non-conservative substitutions are as at one or more of amino acids at positions Asp 52, or His 89 or Ser 271. In one specific form at least amino acid Ser 271 is substituted preferably, non-conservatively. Most preferably the altered toxins with these substitutions act as inhibitors of the enzymatic action of the toxin, and therefore may still bind the target molecule for the toxin.

Altered molecules can be tested by inhibition assays whereby the candidate inhibitor is screened in an in vitro assay with, for example, Vero cells to determine the extent to which toxicity of the subtilase is inhibited.

The altered protein might alternatively encompass changes to the GM2 binding site with reduced binding to GM2.

The invention may also encompass a peptide fragment of the subunit A that includes a sequence comprising one or more of the Asp, His or Ser catalytic motifs set out in FIG. 1. In one form these may reflect the sequence of FIG. 9, alternatively they may include the alternatives as set out in FIG. 1 to reflect sequence of a functional subtilase, or "non-conservative" substitutions to reflect sequence of a non functional subtilase.

It is to be understood that the above peptide fragments do not include the entire Subunit A. Accordingly these fragments may vary in size from between about 4 amino acids to about 300 amino acids. The fragments may be less than 250, 200, 150, 100, 50, or 25 amino acids. In a specific form the peptides may be between 12 and 20 amino acids long. The peptide fragments may form part of a chimera with proteins or peptides derived from proteins other than the subtilase toxin. Such chimeras may form part of a phage display arrangement most particularly designed to facilitate eliciting an immune response, or other chimeric proteins described above. Such peptides may be useful for eliciting a blocking of the toxic effect of the A subunit.

The invention also encompasses peptide fragments of subunit B. Such peptide fragments encompass fragments that bind GM2 but are unable to form a complex with the subunit A.

These peptides may be of prophylactic use in endemic regions.

The invention provides peptide targets for use in assays for the early and rapid diagnosis of infection in vertebrates. Further, the invention provides peptide vaccines for protecting vertebrates against infection by toxin producing bacteria.

It will be understood that the invention also contemplates an isolated polynucleotide encoding the A subunit, as set out in FIG. 9, variant or peptide fragment thereof as set out above.

Similarly the invention also contemplates an isolated polynucleotide encoding the A subunit, as set out in FIG. 9, variant or peptide fragment thereof as set out above.

The polynucleotide may encode both the A and B subunits, variants or peptide fragments thereof.

The invention contemplates a polynucleotide with 95, 90, 80, 70% homology with the corresponding nucleotides of the polynucleotide as the set out in FIG. 9. For nucleic acids, the length of comparison sequences may be at least 50 nucleotides, preferably at least 60 nucleotides, more preferably at least 75 nucleotides, and most preferably 110 nucleotides.

The invention also contemplates polynucleotides that hybridize with the polynucleotide set out in FIG. 9 or fragments of the polynucleotide sequence specific for a toxin with a subtilase domain under stringent hybridisation conditions.

The phrase "stringent hybridization conditions" refers to conditions under which a probe will hybridize to its target subsequence, typically in a complex mixture of nucleic acid, but to no other sequences. Generally, a probe is less than about 1000 nucleotides in length, preferably less than 500 nucleotides in length. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization.

For the purposes of this disclosure, suitable stringent conditions for such hybridizations are those which include a hybridization in a buffer of 40% formamide, 1 M NaCl, 1% SDS at 37° C. and at least one wash in 0.2 times SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

To facilitate recombinant expression, the polynucleotide sequence is often included in a recombinant expression cassette in which the polynucleotide sequence is operably linked to a promoter sequence. This expression cassette may be carried on a self replicating nucleic acid molecule.

The invention also contemplates a recombinant cell carrying the polynucleotide and expressing toxin, variant or peptide fragments thereof.

Preferably the recombinant cell over-expresses the toxin.

The recombinant cells may be eukaryotic or prokaryotic cells, and may be enteric bacteria perhaps gram negative. In the case of safe enteric bacteria expressing non-toxic variants of the present toxin these may be used as a means of inhibiting uptake of the toxin across the gut luminal wall and thus may be given as a preventative agent. Alternatively host cells that are known for over expression of proteins, including animal, plant, yeast or bacterial may simply be used in fermenter systems for harvesting purified protein.

The invention also encompasses an antibody or fragment thereof specific for the toxin. The antibody might specifically be directed against the subunit A or the subunit B. The antibody may be specific for binding to all or part of the three catalytic motifs of the subunit A, namely the Ser, His or Asp motifs. Alternatively it may be specific for the GM2 binding region of subunit B or the region of subunit B involved in complexing with subunit A.

The antibody particularly generally to the toxin or generally to subunit A and B may be polyclonal. The preparation of polyclonal antibodies is well-known to those skilled in the art. See, for example, Green et al., Production of Polyclonal Antisera, in Immunochemical Protocols (Manson, ed.), pages 1–5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference. Methods of obtaining polyclonal antibodies include the step of immunising an animal with either toxin, whole subunit A or subunit B, or variants or peptide fragments thereof. Optionally providing an adjuvant, then after a suitable period harvesting the sera for use as an antibody.

Alternatively the antibody might entail isolating a monoclonal antibody. The method of isolating such an antibody will be understood to include the steps of inoculating an animal with the toxin, subunit, variant or peptide fragment thereof, fusing antibody producing cells with a myeloma cell line and screening for a cell line that produces an antibody reactive with the said toxin, subunit, variant or peptide fragment thereof, and harvesting antibodies from said cell line, testing for inhibition of high affinity binding and testing for inhibition or excitation of function. This may further include making small fragments of antibodies produced by the said cell line capable of binding said toxin, subunit, variant or peptide fragment thereof. The cell line may conveniently be a mouse cell line and the method may include the further step of humanising the said antibody fragments by replacing mouse sequences with human sequences in the non-binding regions.

For preparation of monoclonal antibodies, any technique which provides antibodies produced by continuous cell line cultures can be used. Examples include the hybridoma technique (Kohler and Milstein, 1975), the trioma technique, the human B-cell hybridoma technique (Kozbor et al., 1983). In a preferred method, the antibody producing cells may be fused with a myeloma cell to produce a pool of hybridoma cells which can then be screened for cells that produce the monoclonal antibody.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody.

Antibodies or fragments thereof may be particularly useful in the detection of the presence of enteric bacteria expressing the toxins. They may additionally be used as a therapeutic agent in the event that toxin carrying bacteria are detected.

It is to be understood that where reference is made to a fragment of a monoclonal antibody the term includes, but is not limited to, Fab, Fv and peptide fragments of the monoclonal antibody, and it may also include such fragments when made as part of a different larger peptide or protein, which may be the product of a recombinant vector. Thus the variable region of the respective monoclonal antibody may be cloned and be made part of a hybrid protein with properties appropriate for the therapeutic purposes of the respective agent. Thus for example the monoclonal antibody may be "humanized" by recombining nucleic acid encoding the variable region of the monoclonal antibody with nucleic acid encoding non-variable regions of equine origin in an appropriate expression vector.

The invention might also encompass a method of isolating a small peptide or other small molecule that binds to the active sites of subunit A.

Other compounds capable of binding the toxin, subunit variant or peptide fragment thereof may be isolated by screening for binding to peptides of the present invention. For example, a scramble of randomly synthesised compounds could be passed through a solid matrix to which a peptide of the present invention is bound. Following washing the strongly binding compounds remain and can be eluted and characterised using standard techniques. The screening may also be a competitive binding screen used to identify compounds that bind the toxin, subunit, variant or peptide fragment thereof, in preference to an antibody specific therefore.

The nature of the compounds obtained by screening is not limited and may include, but is not limited to, peptides, oligonucleotides, amino acids, nucleic acids or sugars. The methods used for the binding assay can be any one of the many common techniques known to those skilled in the art. Such methods may include affinity selection chromatography, ultrafiltration assays, the scintillation proximity assay, interfacial optical techniques, the quartz crystal microbalance, the jet ring cell, interferometric assays using porous silicon to immobilise the receptor. Reference to such techniques can be found in Woodbury et al., 1999. By way of example, a scramble of randomly synthesised oligonucleotides could be passed through a solid matrix to which a peptide of the present invention is bound. Following washing the strongly binding oligonucleotides remain and can be eluted under different conditions (salt, pH etc). The sequence can be determined by PCR and tested for inhibition of the action of the toxin.

The present invention may also encompass a method of isolating inhibitors of the binding of AB or B to GM-2.

The present method also encompasses a method of identifying a cytotoxin by its capacity for binding antibodies specific for the exemplified toxin or fragments thereof. The method may comprise the steps of taking a candidate enterotoxigenic bacterial strain or a gastrointestinal sample, checking for the capacity of the strain or fractions thereof or the gastrointestinal sample to react with specific antibodies. This may be performed by conventional ELISA assays or radio labelled antibody-based test. The method may be used for diagnostic purposes or it may be used to screen for other subtilase toxins. The latter may particularly entail using antibodies or fragments thereof directed to the subunit A variants or peptide fragments thereof. The method of identification may also entail using the binding of small molecules referred to above.

Alternatively and probably preferably the invention encompasses a method of nucleic acid amplification utilising primers specific for polynucleotides encoding subunit A, or subunit B above. Methods for nucleic acid amplification are well known in particular the most commonly used, PCR technique. The primers may be of a length in the range of 10 to 30 nucleotides. Examples of suitable primers can be found in Table S2. Other primers suitable for PCR can readily be devised by analysis of the nucleotide sequence set out in FIG. 9.

The method of nucleic acid amplification may be used as a diagnostic method, by testing candidate bacteria or fractions thereof, or a gastrointestinal sample for the presence of nucleic acids encoding subunits A or B or both of the toxin. The primers may also be used in identifying a nucleic acid encoding a toxin with a subtilase domain. In the latter at least one PCR primer specific to the subtilase domain and or catalytic motifs thereof may be preferred.

The present invention also encompasses probes suitable for use in techniques such as Southern Hybridisation. The probes may be any one or more of the polynucleotides of the present invention set out above.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

The invention might in a yet further aspect contemplate the use of GM2 blockers to prevent binding of the toxin to its cell receptor. These preferably take the form of GM2 mimics rather than molecules that bind GM2, because these are less likely to be damaging to the function of GM2. Such blockers might be small molecules delivered systemically for example intra venously, or alternatively delivered orally or otherwise to the gastrointestinal tract. In the latter case they may be delivered either as a matrix to prevent degradation before arrival at the site of protection, typically the small intestine. They may take the form of a chimeric molecule or recombinant organisms carrying recombinant molecules forming GM2 or a GM2 mimic as set forth in Patent specification WO01/19960.

EXAMPLE 1

Here we describe and characterise the prototype of a new $AB_5$ toxin family, which is secreted by a highly virulent O113:H21 Shiga toxigenic Escherichia coli (STEC) strain responsible for an outbreak of hemolytic uremic syndrome (HUS).

We initially demonstrated the production of an additional cytotoxin by this strain (98NK2) by testing fresh culture supernatant for residual cytotoxicity on Vero cells, after absorption with a recombinant E. coli strain that binds and neutralizes all members of the Stx toxin family with high avidity (2,3). The latter construct expresses a modified lipopolysaccharide (LPS), which mimics the Stx receptor (globotriaosyl ceramide; $Gb_3$) (3). The absorbed 98NK2 supernatant exhibited significant residual cytotoxicity, with an endpoint titer of approximately 1,280 50% cytotoxic doses ($CD_{50}$) per ml, compared with 10,240 $CD_{50}$/ml for unabsorbed supernatant. A similar degree of residual cytotoxicity was also observed in supernatant from a derivative of 98NK2 with a deletion mutation in its single Stx-encoding gene (4). The cytopathic effect was maximal after three days incubation and was characterised by rounding of cells, detachment from the substratum, and loss of viability (judged by Trypan blue exclusion).

Figure 5:
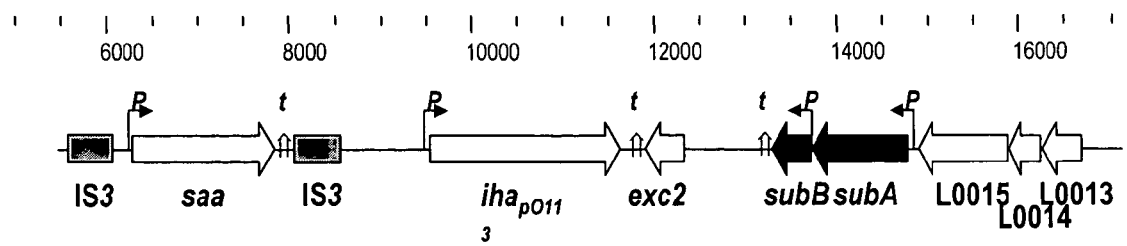
FIG. 5 Map of part of the megaplasmid pO113 from 98NK2. The scale above the figure indicates the corresponding nucleotide numbers in AY423900. The locations of the subA and subB ORFs are shown in solid block arrows; other ORFs are shown as open block arrows, while the grey boxes represent incomplete IS3-like elements. The locations of putative promoters (P) and transcription terminator sequences (t) are also indicated.

To isolate the novel cytotoxin gene, we tested culture supernatants from a 98NK2 cosmid gene bank previously constructed in E. coli DH1 for Vero cytotoxicity. Two cosmid clones with partially overlapping inserts were strongly cytotoxic (endpoint titers were approximately 1,280 $CD_{50}$/ml). The inserts of these cosmids do not contain stx genes, and are derived from a 36.8 kb portion of the 98NK2 megaplasmid pO113, the sequence of which has been deposited in GenBank (accession number AY423900). Genes within the region from nt 5,000 to 17,000 in this sequence are represented in FIG. 5 and described below. Within this region are two closely linked genes which we have designated subA and subB. The subA gene is located on the complementary strand (nt 13,725–14,768 of AY423900) and is preceded by a ribosome binding site (GGAGGAG; nt 14,772–14,778). A putative promoter sequence was identified using the NNPP program (5) with transcription predicted to start at nt 14,831. The subA gene encodes a 347 aa putative secreted protein with a modest degree of similarity to members of the Peptidase_S8 (subtilase) family of serine proteases (pfam00082.8). Its closest bacterial relative is the BA__2875 gene product of Bacillus anthracis (26% identity, 39% similarity over 246 aa). The deduced aa sequence includes a predicted signal peptide cleavage site (determined using the program SignalP V1.1 (6) between $A_2$, and $E_{22}$, which was subsequently confirmed by N-terminal amino acid sequence analysis of isolated protein. PROSITE analysis also indicated that SubA contains three conserved sequence domains, designated the catalytic triad, characteristic of members of the subtilase family (7). The SubA domain sequences match the consensus sequences for the so-called Asp, His and Ser subtilase catalytic domains at 11/12, 10/11 and 10/11 positions, respectively, including the known active site residues (FIG. 1).

The subB gene is 16 nt downstream of subA (nt 13,283–13,708 of AY423900) and is preceded by a ribosome binding site (GGAGG; nt 13,714–13,718). An additional putative promoter sequence was identified upstream of subB with transcription predicted to start at nt 13,774. A potential stem-loop element (ΔG=−19.6 kcal/mol) located immediately downstream of subB (nt 13,176–13,206) may function as a transcription terminator for both subA and subB, since no such elements were identified downstream of subA. The subB gene encodes a 141 aa protein with significant similarities to putative exported proteins from *Yersinia pestis* (YPO0337; 56% identity, 79% similarity over 136 aa) and *Salmonella Typhi* (STY1891; 50% identity, 68% similarity over 117 aa). STY1891 has similarity (30% identity over 101 aa) to the S2 subunit of pertussis toxin, but there is negligible similarity between SubB and the latter. Like SubA, the deduced aa sequence of SubB includes a predicted signal peptide cleavage site between $A_{23}$ and $E_{24}$, which was also confirmed by N-terminal analysis.

To examine the cytotoxicity of their products, we amplified subA, subB, or both subA and subB (subAB) by PCR, subcloned them into pK184, and transformed them into *E. coli* JM109 (2). Culture supernatant of JM109:pK184subAB was strongly cytotoxic for Vero cells (>40,960 $CD_{50}$/ml). As observed with Stx-absorbed 98NK2 culture supernatant, the cytopathic effect was maximal after three days incubation and was characterised by rounding of cells, detachment from the substratum, and loss of viability (FIG. 2). However, culture supernatants of JM109:pK184subA and JM109:pK184subB were not cytotoxic (<10 $CD_{50}$/ml). Western blot analysis of the supernatants using polyclonal murine antisera raised against purified SubA or SubB (2) confirmed that the appropriate clones produced immunoreactive species of the expected sizes (35 kDa and 13 kDa for SubA and SubB, respectively) (online Fig. S2). Cell lysates of the clones were also tested on Vero cells, and that of JM109:pK184subAB was at least 10 times more cytotoxic than the respective culture supernatant, which is consistent with poor release of secreted proteins from the periplasm of *E. coli* K-12 strains. CHO (Chinese hamster ovary) and Hct-8 (human colonic epithelial) cells were also susceptible to the JM109:pK184subAB culture supernatant, albeit to a lesser extent (toxin titers were 2000 $CD_{50}$/ml and 250 $CD_{50}$/ml, respectively).

Figure 6:
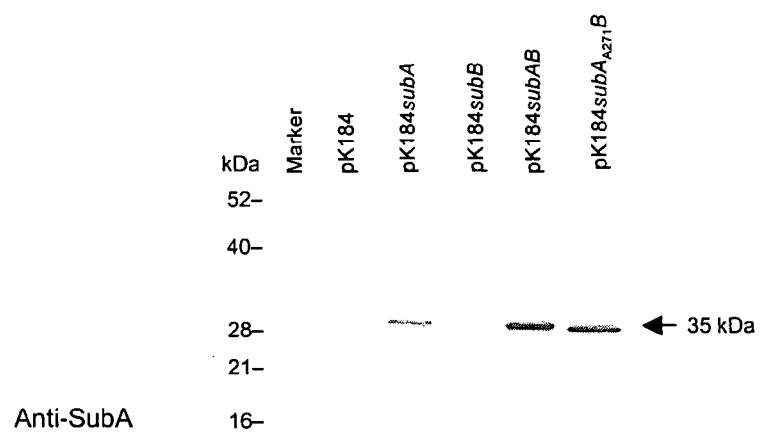
FIG. 6 Western blot analysis of subclones. Culture lysates of E. coli JM109 carrying the indicated plasmids were separated by SDS-PAGE, electroblotted onto nitrocellulose and probed with anti-SubA (upper panel), or anti-SubB (lower panel). The approximate sizes of the immunoreactive species are also indicated.
Figure 6:
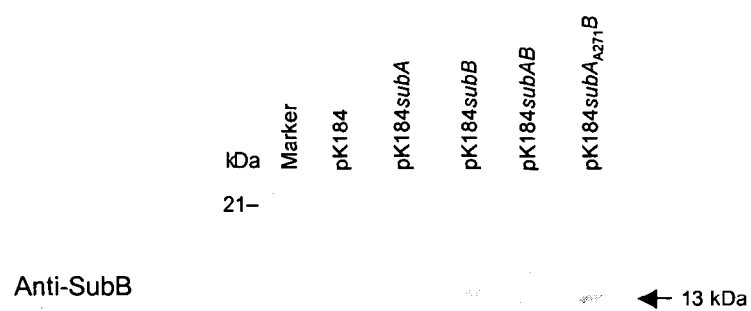

To determine the extent to which the cytotoxicity of SubAB was dependent upon its putative subtilase activity, we constructed a derivative of JM109:pK184subAB with a point mutation such that the predicted active site serine residue (S271) in SubA was altered to alanine (2). Culture supernatant from this derivative (designated JM109:pK184sub$A_{A271}$B) contained both anti-SubA and anti-SubB-reactive species of 35 kDa and 13 kDa, respectively (FIG. 6). However, supernatant and cell lysate fractions from this clone exhibited massively reduced cytotoxicity for Vero cells, with titers of 40 $CD_{50}$/ml and 320 $CD_{50}$/ml, respectively (see also FIG. 2). Thus, the point mutation reduced specific cytotoxicity by greater than 99.9%. We have therefore named the new toxin "Subtilase cytotoxin".

We then confirmed the requirement for both subA and subB for cytotoxicity, by constructing non-polar subA and subB deletion mutants of STEC 98NK2 (2). Replacement of nt 169–908 of the subA coding sequence or nt 83–352 of the subB coding sequence with a 1.6-kb kanamycin-resistance cassette was confirmed by PCR and sequence analysis. The resulting mutants were designated 98NK2_subA and 98NK2ΔsubB, respectively. Western blot analysis confirmed that the former produced SubB, but not SubA, while the latter mutant produced SubA, but not SubB, as expected (9). The cytotoxicity of culture supernatants and cell lysates of 98NK2ΔsubA and 98NK2ΔsubB were then examined using CHO cells, which are susceptible to SubAB, but refractory to the effects of Stx (8). Unlike the wild type 98NK2 extracts, those from either of the mutants had undetectable cytotoxicity. Thus, cytotoxicity requires the presence of both subA and subB. This finding is in accordance with that observed above for cytotoxicity of the JM109 clones expressing subA and/or subB.

We then assessed transcription of subA and subB in 98NK2 and JM109:pK184subAB by real-time reverse-transcription PCR using primer pairs that direct amplification of ~230-bp fragments within subA, within subB or spanning subA and subB (2). RNA templates from both strains yielded similar quantities of RT-PCR product with all three primer sets (9). This indicates that the subA and subB open reading frames are co-transcribed.

Figure 3:
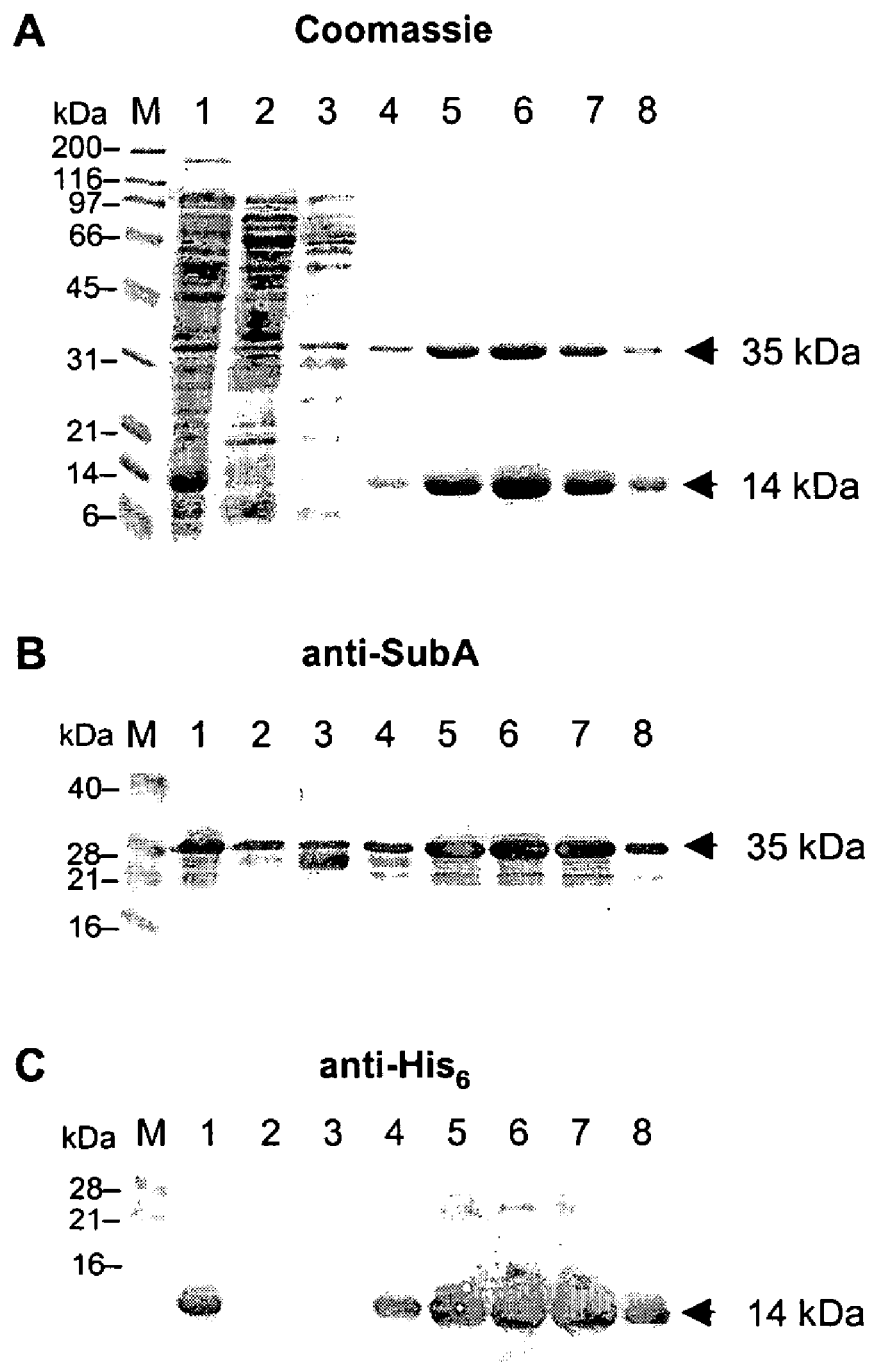
FIGS. 3A–3C. Co-purification of SubA and SubB. Crude lysate of E. Coli Tuner™(DE3):pET-23(+)subAB was applied to a Ni-NTA column, washed and eluted with a linear 0–500 mM imidazole gradient (2). Ten μl aliquots of the original lysate (lane 1) and fractions #3–#9 (lanes 2–8) were separated by SDS-PAGE and either stained with Coomassie blue (upper panel), or electroblotted and probed with polyclonal anti-SubA (middle panel) or monoclonal anti-His$_6$ (lower panel) (2).

The clear requirement for both SubA and SubB for cytotoxicity demonstrated above strongly suggests that the two proteins function together. To examine whether they form an active complex (i.e. an $AB_n$ holotoxin), we subcloned a DNA fragment containing the complete subAB region into the expression vector pET-23(+) such that a $His_6$ tag was fused to the C-terminus of the expressed SubB protein (2). We then subjected lysates of *E. coli* Tuner™ (DE3) expressing this construct to Nickel Nitrilotriacetic acid (Ni-NTA) affinity chromatography (2). Proteins were eluted from the column with a 0–500 mM imidazole gradient, and fractions were analysed by sodium dodecyl sulphate polyacrylamide gel electrophoresis (SDS-PAGE) and Coomassie blue staining, as well as by Western blot using polyclonal anti-SubA or monoclonal antibody to the $His_6$ tag (2) (FIG. 3). The earlier fractions (#3 and #4) contained multiple protein species, including small amounts of anti-SubA-reactive material. However, all the later fractions (#5–#9) contained only two protein species with sizes of 35 kDa and 14 kDa, as predicted for SubA and SubB, respectively (allowing for the extra $His_6$ at the SubB C-terminus). These species reacted strongly with anti-SubA and anti-$His_6$, respectively. Examination of the Coomassie-blue-stained SDS-PAGE gel indicated that the SubA and SubB species were present in apparently constant proportions in each of the fractions (approximately 1:5 on a molar basis, as judged by densitometry). However, the purified SubAB migrated as a single species when subjected to PAGE under non-denaturing conditions, and was not dissociated by treatment with 5% 2-mercaptoethanol (9). Further confirmation of the stoichiometry of the association between SubA and SubB was obtained by subjecting purified SubAB to mild cross-linking conditions prior to SDS-PAGE analysis (2), which indicated that the holotoxin has a molecular size of approximately 105 kDa (9). Collectively, these data indicate that SubA and SubB form a stable complex under non-denaturing conditions, at a ratio of 1:5.

Figure 4:
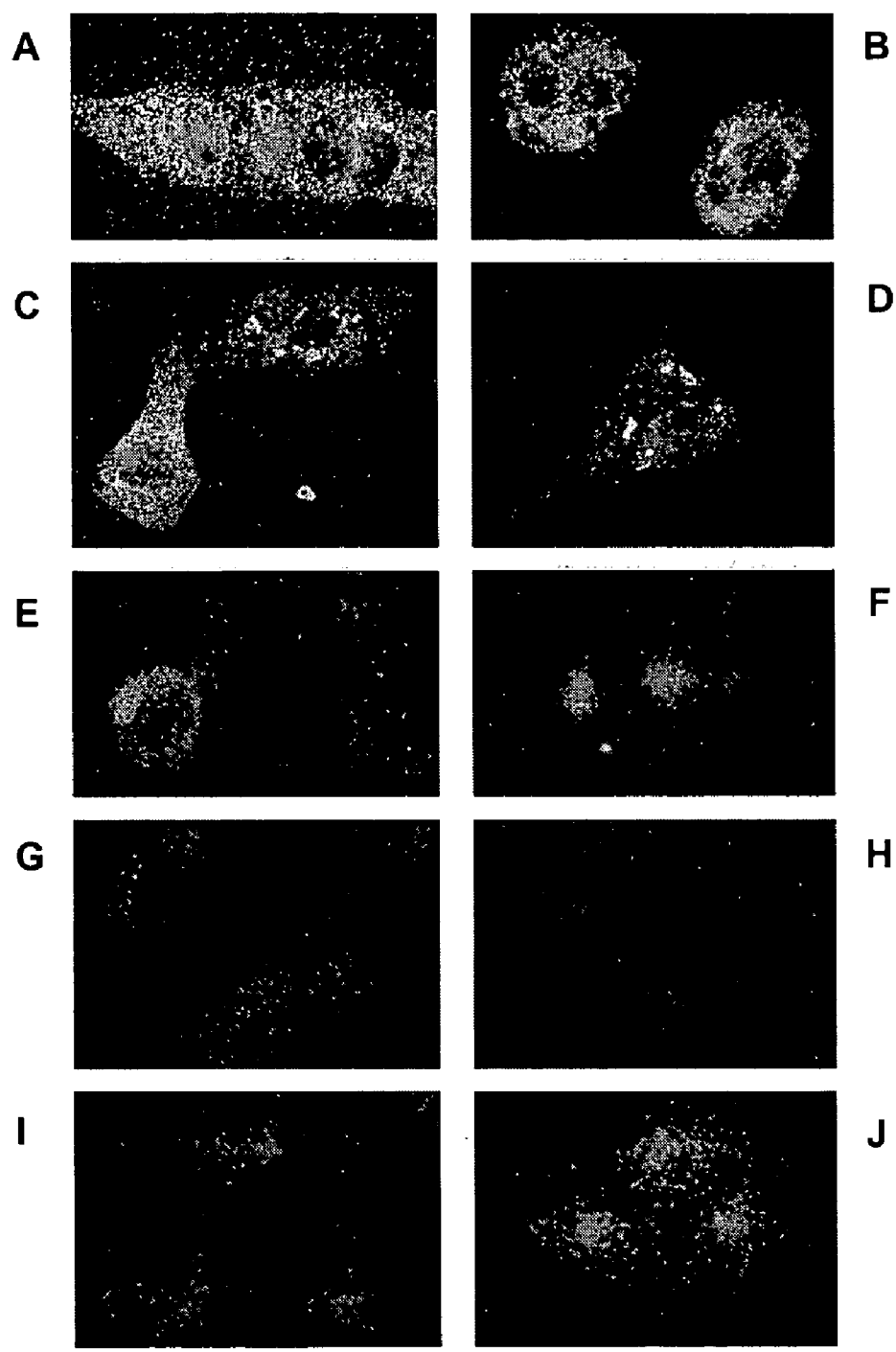
FIGS. 4A–4J Immunofluorescent analysis. Vero cells were treated with purified SubAB for 48 h, fixed, permeabilized (except where indicated), and stained with mouse anti-SubA, anti-SubB, or non-immune serum, followed by goat anti mouse IgG-ALX488 conjugate (2). Panels: A&C, anti-SubA; B&D, anti-SubB; E, anti-SubA (non-permeabilized); F, anti-SubB (non-permeabilized); G, non-immune serum; H, non-immune serum (non-permeabilized); I, anti-SubA without SubAB treatment; J, anti-SubB without SubAB treatment.

Purified SubAB was extraordinarily toxic for Vero cells, with a specific activity>$10^{10}$ $CD_{50}$ per mg. That is, <0.1 pg of SubAB is sufficient to kill at least 50% of the ~$3\times10^4$ Vero cells present in a microtiter plate well. This specific cytotoxicity is approximately 10–100-fold greater than that reported previously for purified Stx and Ctx for HeLa and Y1 adrenal cells, respectively (10, 11). Like the crude extracts tested above, SubAB cytotoxicity was maximal after 72 h incubation of toxin-treated Vero monolayers, and there was little evidence of a cytopathic effect at 24 h, even at high toxin doses. Interestingly, however, if Vero cells were treated with approximately 1000 $CD_{50}$/ml of SubAB for 60 min, followed by removal of the medium, washing of the monolayers three times with fresh medium, and continuation of incubation, significant cytotoxicity was still evident 48–72 h later. This suggests that significant amounts of SubAB were already either tightly bound to the Vero cell surface, or had entered the cells within the first hour. We then examined entry of SubAB into Vero cells directly, by immunofluorescence microscopy (FIG. 4). After 48 h exposure of Vero cells to 1 µg/ml purified SubAB, both anti-SubA- and anti-SubB-reactive material was clearly evident within the cytoplasm. No significant labelling was seen in toxin-treated cells after staining with non-immune mouse serum, or in non-toxin-treated cells stained with the specific antisera. Furthermore, if SubAB-treated cells were not permeabilized prior to staining, very little immunoreactive material was observed. Thus, most of the detectable SubAB appeared to be inside the Vero cells, rather than bound to the outer surface (FIG. 4).

The B pentamers of previously characterised $AB_5$ toxins are known to recognise specific oligosaccharide moieties displayed by host cell glycolipids (1). Differences in receptor specifity of the toxins, as well as in the distribution of the target glycolipids between host species and tissues, has a major impact on host susceptibility and tissue tropism, and the pathology and clinical manifestations of toxin-mediated disease (12). In an attempt to identify candidate glycolipid receptors for SubAB, we absorbed toxin extracts with suspensions of recombinant *E. coli* strains expressing mimics of the oligosaccharide components of glycolipids $Gb_3$, $Gb_4$, lactoneotetraosyl ceramide, and $GM_2$ (3, 13, 14). We then tested the absorbed extracts for Vero cytotoxicity (2). No detectable neutralization of cytotoxicity was observed after absorption with any of the first three constructs, or with the host *E. coli* strain used to express the oligosaccharides. However, absorption with the $GM_2$ mimic neutralized 93.4% of the SubAB activity. Thus, the oligosaccharide expressed by this strain (GalNAcpβ[1→4](NeuAcα[2→3]) Galβ[1→4]Glcβ-) may be a functional receptor for SubAB.

Figure 7:
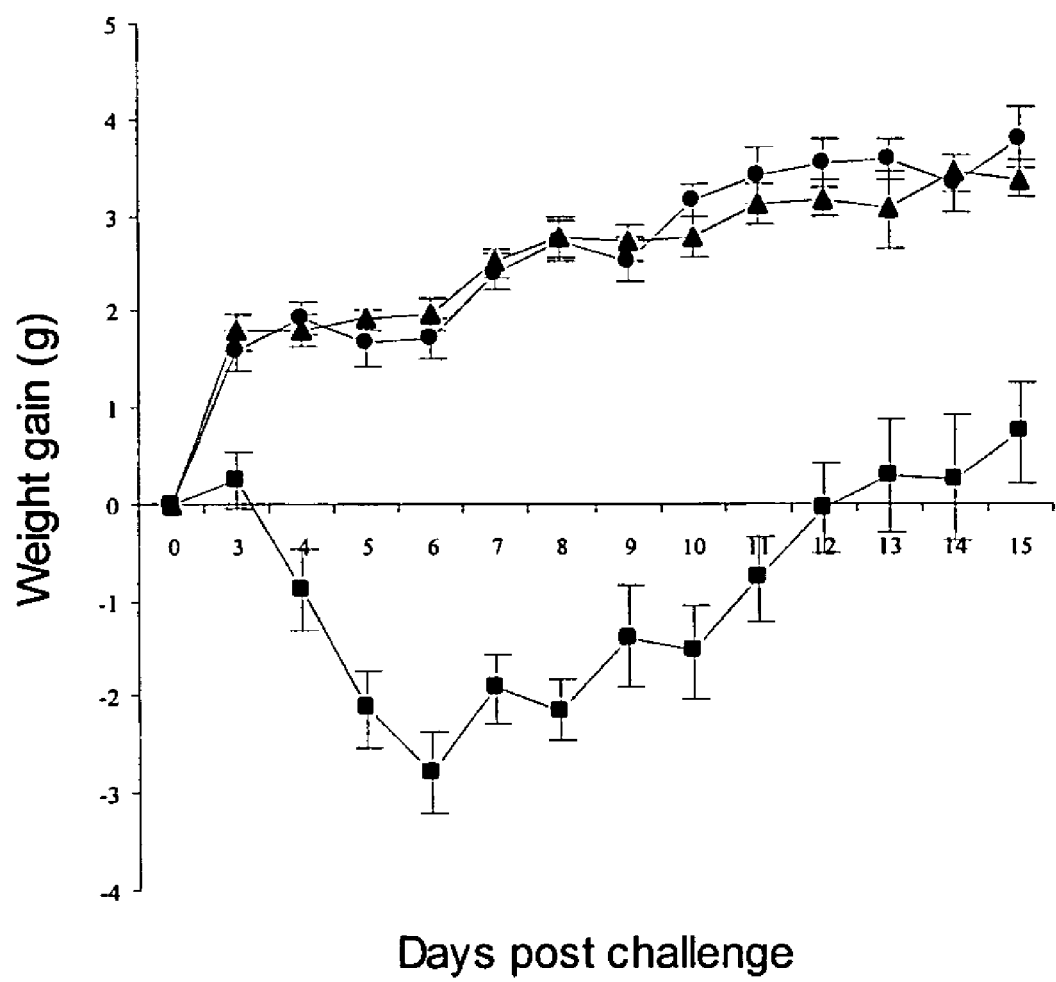
FIG. 7 Weights of mice following oral challenge with SubAB-producing clones. Groups of 8 streptomycin-treated mice were challenged orally with E. coli DH5α$^{SR}$ carrying pK184 (solid circles), pK184subAB (solid squares), or pK184subA$_{A271}$B (solid triangles), as described in the Materials and Methods. Individually identified mice were weighed on day 0 and then daily from day 3. Data are mean weight gain (±standard error), relative to weight of the respective mouse on day 0. The mean weights of mice in the three groups on day 0 were 18.7, 17.8, and 18.0 g, respectively.
Figure 8:
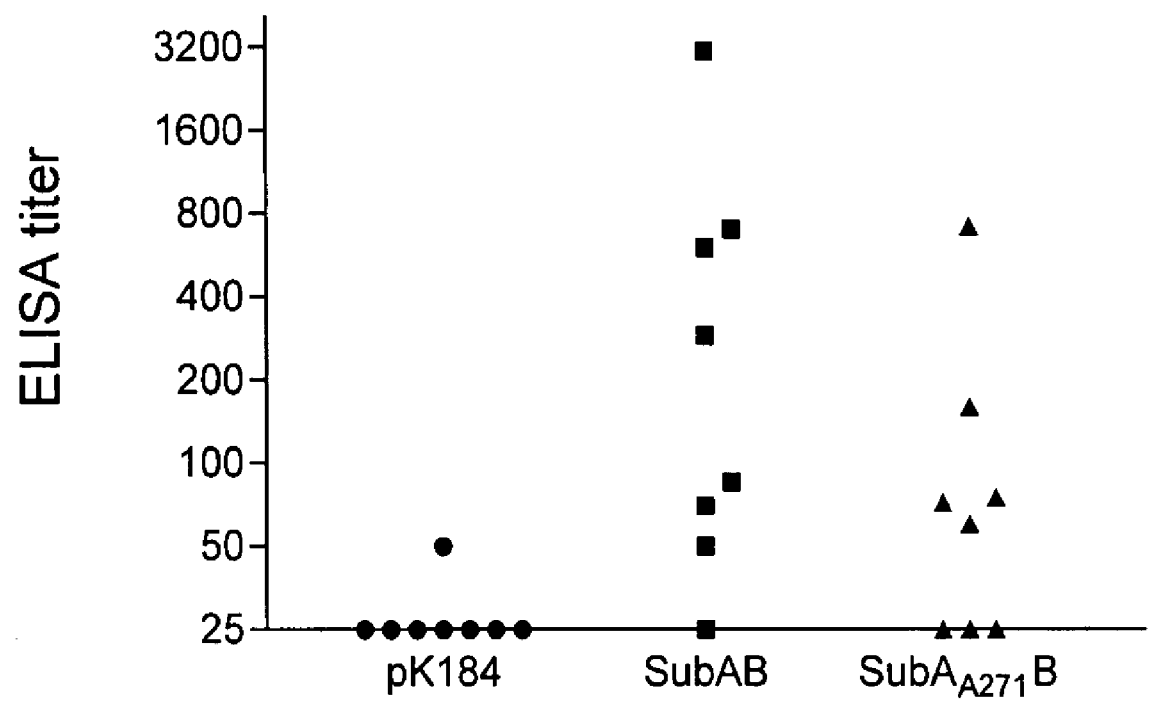

We then examined the in vivo toxicity of SubAB by intraperitoneal injection of pairs of mice with 25 µg, 5 µg, 1 µg, or 200 ng of purified toxin (2). All of the mice died and their survival times were inversely related to dose, ranging from 2 days at 25 µg to 8–10 days at 200 ng. Death was preceded by ataxia and hind limb paralysis, suggestive of neurological involvement. We also challenged groups of streptomycin-treated mice orally with *E. coli* DH5α derivatives carrying pK184, pK184subAB or pK184subA$_{A271}$B. The drinking water was supplemented with streptomycin and kanamycin to inhibit endogenous gut flora and to select for plasmid maintenance. Each of the constructs was maintained at levels of approximately $10^8$14 $10^9$ colony forming units (CFU) per g feces throughout the experiment. During this period, none of the mice exhibited any obvious diarrhoea. The mice challenged with the control strain DH5α: pK184 or DH5α:pK184subA$_{A271}$B remained healthy and active, and gained weight steadily. By day 6 mice in these groups had gained 1.71±0.21, and 1.98±0.18 g, respectively. However, the mice colonized with DH5α:pK184subAB appeared ill and lethargic, and steadily lost body weight during the first 6 days post challenge. By day 6, they had lost 2.78±0.41 g of body weight (FIG. 7), which is equivalent to 15.7% of their mean starting weight on day 0 (17.7 g). Even on day 3, the difference in weight gain between mice challenged with DH5α:pK184subAB and the other two groups was highly significant (P<0.01; Student's t-test). The severe weight loss experienced by the group challenged with the active SubAB-producing clone indicates that toxin delivered via the gut has significant deleterious effects upon the host. Moreover, the fact that the growth of mice challenged with the clone expressing the SubAB protein with the mutation in the active site Ser residue was indistinguishable from that of mice challenged with DH5α:pK184 unequivocally attributes the weight loss to subtilase-mediated cytotoxic activity. Interestingly, the mice challenged with DH5α: pK184subAB started to gain weight from day 7, although they lagged significantly behind the other two groups for the entire duration of the experiment (P<0.001) (FIG. 7). To determine whether seroconversion could account for this apparent recovery, sera collected from each of the mice on day 15 were tested for antibodies to SubAB by ELISA (2). Only one of the mice challenged with DH5α:pK184 had detectable anti-SubAB levels, and this was at the lower limit of detection (titer=50). However, 7 of the 8 mice challenged with DH5α:pK184subAB and of the 8 mice challenged with DH5α:pK184subA$_{A271}$B seroconverted; the highest titers for these groups were 3100 and 720, respectively (FIG. 8).

We then examined the distribution of subAB in other STEC strains isolated from patients with HUS and/or diarrheal disease, or from contaminated food linked to an outbreak of HUS, by PCR and Southern hybridisation analysis (2). The genes are not present in the two published O157:H7 STEC genome sequences (15, 16). However, subAB sequences were present in 32 of 68 other STEC strains tested, including representatives of serogroups O23, O48, O91, O111, O113, O123, O128, O157, OX3, and O non-typable strains. The subAB-positive strains included O111:H⁻ and O157:H⁻ isolates responsible for a large outbreak of HUS (17). The presence of subAB in diverse clinical isolates may be a consequence of the fact that it is located on a plasmid that is capable of conjugative transmission (18). It also raises the possibility that this evidently potent cytotoxin might contribute to pathogenesis of disease in humans and/or animals.

SubAB clearly belongs in a separate family to the other $AB_5$ toxins characterized to date, as it has distinct A subunit enzymic activity (subtilase rather than RNA-N-glycosidase or ADP-ribosylase). Moreover, we have demonstrated that the potent cytotoxicity of SubAB is a consequence of this subtilase activity. The subtilases are a family of serine proteases found in a wide variety of microorganisms (7), but to date, no other members have been shown to have cytotoxic activity. In the present study, we also exposed Vero monolayers to 1 µg/ml purified Subtilisin Carlsberg (a prototype subtilase from *B. licheniformis*; Sigma) and observed no cytotoxic effect whatsoever (9). SubA did not appear to have broad-spectrum proteolytic specificity, and was unable to cleave substrates such as collagen or fibronectin, which might have accounted for the detachment of tissue culture cells from the substratum (9). The presence of SubB was essential for cytotoxicity, and it is likely that this is required for recognition and/or entry of target cells. At present, the intracellular substrate of SubA is unknown, but clearly it is essential for cell survival. Elucidation of this target may enable SubAB, like Ptx, to be used as a tool in cell biology.

The evolutionary origin of Subtilase cytotoxin is unclear. The closest bacterial homologue of SubA is BA_2875 from *B. anthracis*, but examination of the genome sequence of the latter did not reveal the presence of a gene encoding a homologue of SubB in the immediate vicinity. Similarly, examination of the *Y. pestis* and *S. typhi* genome sequences did not reveal the presence of subA-like genes in the vicinity of their respective subB homologues. This study has demonstrated the potentially dire consequences that might arise from genetic rearrangements that bring seemingly innocuous genes into juxtaposition.

In the absence of an animal model that mimics all of the features of STEC disease in humans, the precise contribution of the potent Subtilase cytotoxin to pathogenesis of such disease is difficult to quantify. Stx has long been considered to be a sine qua non of STEC virulence (19,20). However, there has been a report of strains of E. coli O157:H7 and O157:H⁻ that do not produce Stx being associated with cases of human gastrointestinal disease, including HUS (21). Thus, the presence of subAB in diverse STEC isolates from cases of severe human disease demands rigorous investigation of the toxin's biological effects in vitro and in vivo, including the possibility that SubAB and Stx might act synergistically. The fact that subAB is carried on a mobile DNA element, and its presence already in a diverse range of E. coli O:H serotypes also raises the possibility of further transmission to other enteric bacteria. If an unequivocal role for Subtilase cytotoxin in disease in humans or animals becomes apparent, the work presented here will provide the foundation for effective diagnostic, therapeutic and preventative strategies. We have reported PCR primers suitable for use in direct detection of subAB-carrying bacteria in complex clinical and environmental samples. By demonstrating that a $Ser_{27}1$-Ala substitution in SubA virtually abolishes cytotoxicity, we have identified a safe candidate vaccine antigen. Finally, by demonstrating that a harmless strain of E. coli expressing a mimic of the glycolipid $GM_2$ binds and/or neutralizes SubAB, we have identified a means of absorbing Subtilase cytotoxin in the gut of infected individuals. We have previously demonstrated the in vivo efficacy of this receptor-mimic therapeutic strategy using a mimic of the Stx receptor (3).

Materials and Methods

Bacterial Strains, Plasmids and Oligonucleotides. Bacterial strains, plasmids and oligonucleotides used in this study are listed in Tables S1 and S2. The O113:H21 STEC strain 98NK2 was isolated from a patient with haemolytic uremic syndrome at the Women's and Children's Hospital (WCH), South Australia, as previously described (12). Other clinical STEC strains used in this study were also isolated at WCH. All E. coli strains were routinely grown in Luria-Bertani (LB) medium (23) with or without 1.5% Bacto-Agar. Where appropriate, ampicillin or kanamycin were added to growth media at a concentration of 50 µg/ml.

Toxin adsorption/neutralization with receptor mimic bacteria. E. coli CWG308:pJCP-Gb₃, expressing a modified lipopolysaccharide which mimics the Stx receptor $Gb_3$ (24) was grown overnight in LB broth supplemented with 20 µg/ml IPTG, and 50 µg/ml kanamycin. Cells were harvested by centrifugation, washed and resuspended in phosphate-buffered saline (PBS) at a density of $10^9$ CFU/ml. 98NK2 culture supernatant (250 µl) was incubated with 500 µl of this suspension for 1 hour at 37° C. with gentle agitation. The mixture was then centrifuged, filter-sterilized, and assayed for cytotoxicity. The same procedure was also used to compare toxin neutralization using derivatives of E. coli CWG308 expressing mimics of $Gb_4$, lactoneotetraose and $GM_2$ (25, 26). Neutralization of cytotoxicity (%) was calculated as described previously (24).

Cell Culture and Cytotoxicity Assays. All tissue culture media and reagents were obtained from Gibco BRL-Life Technologies (Grand Island, N.Y., USA). Vero (African green monkey kidney) Vero cells were grown at 37° C. in Dulbecco's modified Eagle's medium (DMEM) supplemented with 10% heat inactivated FCS, 50 IU penicillin and 50 µg streptomycin per ml, unless otherwise indicated. Chinese hamster ovary (CHO) cells were grown in Ham's F12 medium, while Hct-8 cells were grown in RPMI 1640 medium. For cytotoxicity assays, cells were seeded into 96 well flat bottom trays and incubated overnight at 37° C. until confluent. Confluent monolayers were washed twice with PBS, then treated with 50 µl filter sterilized toxin extracts which had been serially diluted in the appropriate tissue culture medium (without FCS), and incubated at 37° C. for 30 min. After incubation, 150 µl of medium supplemented with 2% FCS was added per well. Cytotoxicity was assessed microscopically after 3 days of incubation at 37° C. The toxin titer was defined as the reciprocal of the maximum dilution producing a cytopathic effect on at least 50% of the cells in each well ($CD_5O$/ml).

Manipulation and Analysis of DNA. Routine DNA manipulations (restriction digestion, agarose gel electrophoresis, ligation, transformation of E. coli, Southern hybridization analysis, etc.) were carried out essentially as described previously (23). For DNA sequencing, plasmid DNA template was purified using a QIAPrep Spin miniprep kit (Qiagen, Germany). The sequence of both strands was then determined using dye-terminator chemistry and either universal M13 sequencing primers or custom-made oligonucleotide primers, on an Applied Biosystems model 3700 automated DNA sequencer.

Subcloning of subAB. The subA, subB, or both subA and subB (subAB) open reading frames were amplified from 98NK2 genomic DNA by PCR using primer pairs SubAF/SubAR, SubBF/SubBR, and SubAF/SubBR (Table S2), respectively, using the Expand High Fidelity PCR system (Roche Molecular Diagnostics, Germany), according to the manufacturer's instructions. The purified PCR products were then blunt-cloned into SmaI-digested pK184, and transformed into E. coli JM109. Recombinant plasmids were extracted from transformants and confirmed by sequence analysis. In all cases, the inserts were in the same orientation as the vector lac promoter.

Preparation of antisera to SubA and SubB. In order to raise specific antisera, we first purified SubA and SubB using a QIAexpress kit (Qiagen, Germany). The subA and subB open reading frames, without the 5' signal peptide-encoding regions, were amplified by high fidelity PCR using 98NK2 genomic DNA template and primer pairs pQEsubAF/pQEsubAR and pQEsubBF/pQEsubBR, respectively (Table S2). Purified PCR products were digested with BamHI/SacI, or SphI/SacI, respectively, ligated with similarly digested pQE30, and transformed into E. coli M15. Correct insertion of the genes into the vector, such that the recombinant plasmids encode derivatives of SubA and SubB with $His_6$ tags at their N termini, was confirmed by sequence analysis. For purification of $His_6$-fusion proteins, transformants were grown in 1 liter LB supplemented with 50 µg/ml ampicillin and when the culture reached an $A_{600}$ of 0.5, the culture was induced with 2 mM IPTG and incubated for a further 3 h. Cells were harvested by centrifugation, resuspended in 24 ml buffer A (6M guanidine-HCl, 0.1 M $NaH_2PO_4$, 10 mM Tris, pH 8.0) and stirred at room temperature for 1 h. Cell debris was removed by centrifugation at 10,000×g for 25 min at 4° C. The supernatant was then loaded (at a rate of 15 ml/h) onto a 2 ml column of Ni-NTA resin (ProBond, Invitrogen), which had been pre-equilibrated with 20 ml buffer A supplemented with 0.5 M NaCl and 15 mM imidazole. The column was then washed with 40 ml buffer A, followed by 20 ml buffer B (8M urea, 0.1 M $NaH_2PO_4$, 10 mM Tris, pH 8.0), and then 16 ml buffer C (8M urea, 0.1 M $NaH_2PO_4$, 10 mM Tris, pH 6.3), supplemented with 0.25 M NaCl and 5 mM imidazole. The fusion proteins were then eluted with a 30 ml gradient of 0–500 mM imidazole in buffer C; 3 ml fractions were collected and analysed by SDS-PAGE. Peak fractions were pooled and the denatured SubA and SubB were refolded by dialysis against 100 ml buffer B to which 1 liter of PBS was added dropwise at a rate of 60 ml/h. This was followed by dialysis against two changes of PBS. The purified SubA and SubB were >95% pure, as judged by SDS-PAGE after staining with Coomassie brilliant blue R250.

Balb/C mice were then immunized by intraperitoneal injection of three 10 μg doses of purified SubA or SubB in 0.2 ml PBS containing 5 μg alum adjuvant (Imjectalum; Pierce, Rockford, Ill., USA) at two week intervals. Mice were exsanguinated by cardiac puncture one week after the third immunization, and pooled antisera were stored in aliquots at −15° C.

Western blot analysis. Crude lysates or culture supernatants of E. coli strains, or purified proteins were separated by SDS-PAGE (27), and antigens were electrophoretically transferred onto nitrocellulose filters (28). Filters were probed with polyclonal mouse anti-SubA or anti-SubB sera (used at a dilution of 1:5000), or monoclonal antibody to $His_6$ (Qiagen), followed by goat anti-mouse IgG conjugated to alkaline phosphatase (BioRad Laboratories). Labelled bands were visualized using a chromogenic nitro-blue tetrazolium/X-phosphate substrate system (Roche Molecular Diagnostics).

Site-directed mutagenesis of subA. A derivative of JM109:pK184subAB with a point mutation such that the predicted active site serine residue (S271) in SubA was altered to alanine was constructed by overlap extension PCR mutagenesis. This involved high fidelity PCR amplification of pK184subAB DNA using primer pairs SubAF/SubOLR and SubOLF/SubBR (Table S2). This generates two fragments with the necessary mutation in codon 271 of SubA incorporated into the overlapping region by the SubOLR and SubOLF primers. The two separate PCR products were purified, mixed together and the complete subAB region reamplified using primer pair SubAF/SubBR. The resultant PCR product was blunt-cloned into SmaI-digested pK184, and transformed into E. coli JM109. Recombinant plasmids were purified from the resultant transformants and subjected to sequence analysis to confirm that the mutation had been introduced, and that the modified subAB operon was inserted in the vector in the same orientation as in pK184subAB. This construct was designated $pK184subA_{A271}B$.

Construction of subA and subB deletion derivatives of STEC 98NK2. Non-polar subA and subB deletion mutants of STEC 98NK2 were constructed using the lambda Red recombinase system (29). This involved high fidelity PCR amplification of the kanamycin resistance cartridge in pKD4 using primer pairs (SubAmutF/SubAmutR and SubBmutF/SubBmutR; Table S2) incorporating the direct repeated FRT (FLP recognition target) common priming site and sequences derived from the 5' and 3' ends of the subA or subB genes, respectively. The resultant linear fragments were electroporated into 98NK2 carrying the temperature-sensitive plasmid pKD46, which encodes the lambda recombinase. Allelic replacement mutants were selected on LB-kanamycin plates at 37° C. Replacement of nt 169–908 of the subA coding sequence or nt 83–352 of subB with the kanamycin resistance cartridge was confirmed by PCR and sequence analysis of the mutants, which were designated 98NK2ΔsubA and 98NK2ΔsubB, respectively.

RNA extraction. RNA was extracted from log-phase LB cultures of 98NK2 using Trizol reagent, according to the manufacturer's instructions (Life Technologies, Grand Island, N.Y., USA). RNA was precipitated in ⅒ volume sodium acetate (pH 4.8) and 2 volumes 100% ethanol at −80° C. overnight. RNA was then pelleted by centrifugation at 12,000×g for 30 min at 4° C., washed in 70% ethanol, and resuspended in nuclease-free water. RNasein ribonuclease inhibitor (Promega, Madison, Wis., USA) was then added to the samples. Contaminating DNA was digested with RQ1 RNase-free DNase, followed by DNase stop solution, according to the manufacturers instructions (Promega, Madison, Wis., USA).

Real time reverse transcription PCR. The comparative levels of subA, subB and subAB transcripts were determined using quantitative real time reverse transcription PCR (RT-PCR), using primer pairs RTsubAF/RTsubAR, RTsubBF/RTsubBR, and RTsubABF/RTsubABR, respectively (Table S2). These direct amplification of 220-bp, 238-bp and 232-bp fragments within subA, within subB, or spanning subA and subB, respectively. RT-PCR was performed using the one-step access RT-PCR system (Promega) according to the manufacturer's instructions. Each reaction was performed in a final volume of 20 μl, containing 20 nmol of each oligonucleotide, and a ¹/₂₀,₀₀₀ dilution of Sybr green I nucleic acid stain (Molecular Probes). The quantitative RT-PCR was performed on a Rotorgene RG-2000 cycler (Corbett Research, Mortlake, NSW, Australia) and included the following steps: 45 min of reverse transcription at 48° C., followed by 2 min denaturation at 94° C., and then 40 cycles of amplification using 94° C. for 30 seconds, 56° C. for 30 seconds, and 72° C. for 45 seconds.

Co-purification of SubAB. In order to purify the SubAB holotoxin, the complete subAB coding region was amplified by high fidelity PCR using 98NK2 DNA template and the primer pair pETsubAF/pETsubBR (Table S2). The resultant PCR product was digested with BamHI and XhoI, ligated with similarly digested pET-23(+), and transformed into E. coli Tuner™(DE3). This results in IPTG-dependent production of both the SubA and SubB proteins (including their respective signal peptides), but with a $His_6$ tag fused to the C-terminus of SubB. Correct insertion of the genes into the vector was confirmed by sequence analysis. Cells were grown in 1 liter LB supplemented with 50 μg/ml ampicillin and when the culture reached an $A_{600}$ of 0.5, the culture was induced with 5 mM IPTG and incubated for a further 3 h. Cells were harvested by centrifugation, resuspended in 20 ml loading buffer (50 mM sodium phosphate, 300 mM NaCl, pH 8.0) and lysed in a French pressure cell. Cell debris was removed by centrifugation at 100,000×g for 1 h at 4° C. The supernatant was then loaded onto a 2 ml column of Ni-NTA resin, which had been pre-equilibrated with 20 ml loading buffer. The column was then washed with 40 ml wash buffer (50 mM sodium phosphate, 300 mM NaCl, 10% glycerol, pH 6.0). Bound proteins were then eluted with a 30 ml gradient of 0–500 mM imidazole in wash buffer; 3 ml fractions were collected and analysed by SDS-PAGE.

Cross-linking of SubAB. Purified SubAB was treated with 0.5% formaldehyde for 60 min at room temperature, and then heated at 60° C. for 10 min prior to SDS-PAGE analysis to determine the size of the holotoxin. Purified E. coli heat labile enterotoxin (26), which is known to have $AB_5$ stoichiometry, was treated and analysed in parallel.

Immunofluorescence. Vero cells were grown on glass coverslips in 24 well tissue culture plates and treated with or without 1 μg per ml purified SubAB. After 48 h, cells were fixed with 4% formaldehyde in PBS for 10 min, and in some cases permeabilized with 0.1% Triton X-100. Coverslips were then washed in PBS, and blocked with 20% FCS in PBS for 1 h at 37° C. They were then treated with either anti-SubA, anti-SubB, or non-immune mouse serum (diluted 1:800 in PBS/10% FCS) for 2 h at 37° C. After three washes with PBS, the coverslips were reacted with goat anti-mouse IgG-ALX488 conjugate (Molecular Probes), diluted 1:250 in PBS/10% FCS for 30 min at 37° C. The coverslips were then washed three times with PBS, twice with water, dried, and mounted on glass slides using 3 μl Mowiol solution with anti-bleach. Slides were examined using an Olympus IMT-2 microscope equipped with epi-fluorescence optics, using a 60×oil-immersion apochromatic objective.

Distribution of subAB. Crude lysates of STEC strains (all clinical isolates) were subjected to PCR amplification using primer pair RTsubABF/RTsubABR (Table S2). Alternatively, HindIII digests of genomic DNA purified from the STEC strains were transferred to nylon membranes and probed at high stringency with a digoxigenin-labelled subAB DNA fragment obtained by PCR amplification of pK184subAB using primer pair subAF/SubBR (Table S2).

In vivo studies. Animal experimentation was conducted in accordance with the Australian Code of Practice for the Care and Use of Animals for Scientific Purposes, and was approved by the Animal Ethics Committee of the University of Adelaide. Groups of eight 5–6 week old balb/C mice, each weighing approximately 17–19 g, were given oral streptomycin (5 mg/ml in drinking water) for 24 hours before oral challenge with approximately $10^8$ CFU of a streptomycin-resistant derivative of E. coli DH5α (DH5α$^{SR}$) carrying pK184, pK184subAB or pK184subA$_{A271}$B, suspended in 60 μl of 20% sucrose, 10% NaHCO$_3$. Drinking water was then supplemented with streptomycin (5 mg/ml) and kanamycin (100 μg/ml). Mice were weighed daily, and numbers of the recombinant bacteria in fecal samples from each group were monitored by plating on LB agar supplemented with 50 μg/ml streptomycin and 50 μg/ml kanamycin. Alternatively, pairs of balb/C mice were injected intraperitoneally with either 25 μg, 5 μg, 1 μg, or 200 ng purified SubAB in 0.1 ml PBS.

Anti-SubAB ELISA assay. Antibodies to SubAB were measured by ELISA using 96-well Costar PVC plates which were coated overnight at 4° C. with 100 μl of 5 μg/ml purified SubAB in TBS (25 mM Tris-HCl, 132 mM NaCl, pH 7.5). Plates were then washed with TBS-0.1% Triton X-100, and blocked with TBS-0.05% Tween-20, 0.02% bovine serum albumin (TBS-Tween-BSA) for 2 h at 37° C. Plates were washed again and then incubated for 4 h at 37° C. with 100 μl serial dilutions of mouse serum in TBS-Tween-BSA, commencing at 1:50. Plates were then washed and incubated with goat anti-mouse IgG alkaline phosphatase conjugate (EIA grade; Bio-Rad Laboratories, CA), diluted 1:15,000 in TBS-Tween-BSA for 2 h at 37° C. Plates were then washed and developed with 1 mg/ml p-nitrophenyl phosphate substrate (in 12.5 mM Triethanolamine, 135 mM NaCl, 0.02% BSA, 1 mM MgCl$_2$, 2.5 μM ZnCl$_2$, pH 7.6) for 2 h at 37° C., after which Absorbance at 450 nm was determined. Absorbance above background was plotted against serum dilution, and the ELISA titer was defined as the reciprocal of the serum dilution resulting in an $A_{450}$ reading of 0.2 above background.

Description of genes in the region of pO113 associated with cytotoxicity. The region immediately 3' to that shown in FIG. 5 contains a previously described type IV pilus biosynthesis locus (30). The region of pO113 shown in FIG. 5 includes the saa gene, which is flanked by imperfect IS3-like elements, and encodes a previously-characterised outer membrane protein implicated in adherence to epithelial cells (31). It also contains a gene (designated iha$_{pO113}$) which encodes a protein with 94% identity to Iha from E. coli O157:H7 (AF126104) and a ferric siderophore receptor from uropathogenic E. coli (AF081285), as well as a gene with significant similarity to the entry exclusion protein 2 gene exc2 of plasmid ColE (NC_001371). At the 3' end of the region shown in FIG. 5 are three open reading frames encoding proteins related to L0013-, L0014- and L0015-like proteins from E. coli O157:H7 (NC_002655). The two closely linked genes subA and subB are located between 10015 and exc2.

Tables

TABLE S1

Bacterial strains and plasmids

| Bacterial strain or plasmid | Relevant characteristics | Ref. or source |
|---|---|---|
| E. coli | | |
| 98NK2 | O113:H21 Stx2-producing STEC | (22) |
| JM109 | K-12 cloning host | (32) |
| M15 | expression host for pQE vectors | QIAgen, Germany |
| Tuner ™(DE3) | expression host for pET vectors | Novagen, USA |
| DH5α$^{SR}$ | Streptomycin resistant DH5α | (33) |
| Plasmids | | |
| pK184 | | (34) |
| pQE30 | | QIAgen |
| pET-23(+) | | Novagen |

TABLE S2

Oligonucleotides

| Name | Sequence (5'-3') | Restriction sites |
|---|---|---|
| SubAF | GTACGGACTAACAGGGAACTG (SEQ ID NO. 4) | |
| SubAR | ATCGTCATATGCACCTCCG (SEQ ID NO. 5) | |
| SubBF | GTAGATAAAGTGACAGAAGGG (SEQ ID NO. 6) | |
| SubBR | GCAAAAGCCTTCGTGTAGTC (SEQ ID NO. 7) | |

TABLE S2-continued

Oligonucleotides

| Name | Sequence (5'–3') | Restriction sites |
|---|---|---|
| SubOLF | GGTAGCGGAACGGCAGAAGCAACAGCTATAG (SEQ ID NO. 8) | |
| SubOLR | AGCTGTTGCTTCTGCCGTTCCGCTACCAGTCC (SEQ ID NO. 9) | |
| SubAmutF | TACCCCAGTGGTCGTATCTGTTGTTGATTCCGGAGTGGCAGTGTAGGCTGGAGCTGCTTC (SEQ ID NO. 10) | |
| SubAmutR | TGTCACTTTATCTACAAGTGAAGGGTATTTATCTGCAGACCATATGAATATCCTCCTTAG (SEQ ID NO. 11) | |
| SubBmutF | TGTCTATCCCTTAATCCAGCTATGGCTGAGTGGACTGGTGGTGTAGGCTGGAGCTGCTTC (SEQ ID NO. 12) | |
| SubBmutR | ATTCTGTCGATGTGGTGCAGGTTGATAACCCAACAAGAGCACATATGAATATCCTCCTTAG (SEQ ID NO. 13) | |
| pQEsubAF | CCCTGGGGATCCGATGCAATTGGTCTGACAG (SEQ ID NO. 14) | BamHI |
| pQEsubAR | GTTCGAGCTCACTCATCCTTCCCTGACG (SEQ ID NO. 15) | SacI |
| pQEsubBF | GGTGGCATGCGGGGATGGCATGTTTTCAG (SEQ ID NO. 16) | SphI |
| pQEsubBR | CTTAGAGCTCCTTTTTCCTGTCAGGACC (SEQ ID NO. 17) | SacI |
| pETsubAF | TTGTAAGGATCCGGAGGAGCTTATGCTTAAG (SEQ ID NO. 18) | BamHI |
| pETsubBR | GATTATCTCGAGTGAGTTCTTTTTCCTGTCAGG (SEQ ID NO. 19) | XhoI |
| RTsubAF | CGAATGTTTTTCTTGCTCCAG (SEQ ID NO. 20) | |
| RTsubAR | ACACTGCTGACAGGATGATAAG (SEQ ID NO. 21) | |
| RTsubBF | GTTTTCAGGCGTTGTTATTACC (SEQ ID NO. 22) | |
| RTsubBR | CACAAAAGGTGGATACGTCC (SEQ ID NO. 23) | |
| RTsubABF | GCAGATAAATACCCTTCACTTG (SEQ ID NO. 24) | |
| RTsubAB-1R | ATCACCAGTCCACTCAGCC (SEQ ID NO. 25) | |

EXAMPLE 2

Generation of Antibody Antagonists

Monoclonal antibodies can be generated by immunizing with toxin, subunits A or B or variant or peptide fragment thereof. After specificity controls demonstrate specific binding to the subunits A or B or variant or peptide fragment thereof the antibodies may be selected for inhibiting the cytotoxic effect of the toxin on verocells or the capacity of the toxin to bind $GM_2$. Once an appropriate monoclonal antibody has been identified and shown to have an inhibitory effect, smaller fragments may be generated; e.g. F(ab)$_2$, Fab and ultimately Fv. By utilising molecular biology techniques a single chain Fv fragment can be constructed (Hv-Lv). This would be an inhibitory peptide.

EXAMPLE 3

Generation of Peptide Antagonists

Short peptides of similar sequences to the toxin, subunits A or B or variant or peptide fragment thereof may be synthesized that block toxin interaction with its target.

EXAMPLE 4

Generation of Oligonucleotide Antagonists

A large pool of randomly synthesized oligonuclotides can be passed through a toxin, subunits A or B or variant or peptide fragment thereof immobilized on a solid matrix (Bock et al., 1992, —which reference is incorporated herein). Following washing, the strongly binding oligonucleotides remain and can then be eluted under different conditions (salt, pH etc). The sequence can then be determined by PCR and tested for inhibition of toxin activity.

Various features of the invention have been particularly shown and described in connection with the exemplified embodiments of the invention, however, it must be understood that these particular arrangements merely illustrate and that the invention is not limited thereto and can include various modifications falling within the spirit and scope of the invention.

REFERENCES

1. E. Fan, E. A. Merritt, C. L. M. J. Verlinde, W. G. J. Hol, *Curr. Opin. Struct. Biol.* 10, 680 (2000).
2. Materials and methods are available as supporting material on *Science* Online.
3. A. W. Paton, R. Morona, J. C. Paton, *Nature Med.* 6, 165 (2000).
4. T. J. Rogers, A. W. Paton, S. R. McColl, J. C. Paton, *Infect. Immun.* 71, 5623 (2003).
5. M. G. Reese, N. L. Harris, F. H. Eeckman, in *Biocomputing: Proceedings of the* 1996 *Pacific Symposium*, L. Hunter, T. E. Klein, Eds. (World Scientific Publishing Co., Singapore, 1996).
6. H. Nielsen, J. Engelbrecht, S. Brunak, G. von Heijne, *Protein Eng.* 10, 1 (1997).
7. R. J. Siezen, W. M. de Vos, J. A. M. Leunissen, B. W. Dijkstra, *Protein Eng.* 4, 719 (1991).
8. M. S. Jacewicz et al., *J. Infect. Dis.* 169, 538 (1994).
9. A. W. Paton, P. Srimanote, U. M. Talbot, J. C. Paton, result not shown.
10. A. D. O'Brien, G. D. LaVeck, *Infect. Immun.* 40, 675 (1983).
11. J. D. Clements, R. A. Finkelstein, *Infect. Immun.* 24, 760 (1979).
12. K. Karlsson, *Mol. Microbiol.* 19, 1 (1998).
13. A. W. Paton, R. Morona, J. C. Paton. Infect. Immun. 69, 1967 (2001).
14. A. W. Paton, R. Morona, M. P. Jennings, A. Focareta, J. C. Paton. In preparation.
15. N. T. Perna et al., *Nature* 409, 529 (2001).
16. T. Hayashi et al., *DNA Res.* 8, 11 (2001).
17. A. W. Paton et al., *J. Clin. Microbiol.* 34, 1622 (1996).
18. P. Srimanote, A. W. Paton, J. C. Paton, *Infect. Immun.* 70, 3094 (2002).
19. M. A. Karmali, *Clin. Microbiol. Rev.* 2, 15 (1989).
20. J. C. Paton, A. W. Paton, *Clin. Microbiol. Rev.* 11, 450 (1998).
21. H. Schmidt, J. Scheef, H. I. Huppertz, M. Frosch, H. Karch. *J. Clin. Microbiol.* 37, 3491 (1999).
22. A. W. Paton, M. C. Woodrow, R. M. Doyle, J. A. Lanser, J. C. Paton, *J. Clin. Microbiol.* 37, 3357 (1999).
23. T. Maniatis, E. F. Fritsch, J. Sambrook. *Molecular cloning: a laboratory manual* (Cold Spring Harbor Laboratory, N.Y., 1982).
24. A. W. Paton, R. Morona, J. C. Paton, *Nature Med.* 6, 165 (2000).
25. A. W. Paton, R. Morona, J. C. Paton. Infect. Immun. 69, 1967 (2001).
26. A. W. Paton, R. Morona, M. P. Jennings, A. Focareta, J. C. Paton. In preparation.
27. U. K. Laemmli, *Nature* 227, 680 (1970).
28. H. Towbin, T. Staehelin, J. Gordon, *Proc. Natl. Acad. Sci. USA.* 76, 4350 (1979).
29. K. A. Datsenko, B. L. Wanner, *Proc. Natl. Acad. Sci. USA.* 97, 6640 (2000).
30. P. Srimanote, A. W. Paton, J. C. Paton, *Infect. Immun.* 70, 3094 (2002).
31. Paton A. W., Srimanote, P., Woodrow, M. C., & Paton, J. C. (2001) *Infect. Immun.* 69, 6999–7009.
32. C. Yanisch-Pyrron, J. Vieira, J. Messing, *Gene* 33, 103 (1985).
33. A. W. Paton, A. J. Bourne, P. A. Manning, J. C. Paton, *Infect. Immun.* 63, 2450 (1995).
34. M. G. Jobling, R. K. Holmes, *Nucleic Acids Res.* 18, 5315(1990).

The invention claimed is:

1. An isolated bacterial $AB_5$ toxin, or subunits thereof, the A subunit having a subtilase domain, the B subunit having the ability to recognize cell surface oligosaccharide component GM2(GalNAcβ[1→4](NeuAcα[2→3]Galβ[1→4Glcβ-), said toxin being cytotoxic to Vero Cells.

2. The isolated toxin of claim 1 wherein the A subunit has a molecular weight of about 35 kD estimated on SDS PAGE.

3. The isolated toxin of claim 1 wherein the B subunits each have a molecular weight of about 13 kD estimated on SDS PAGE.

4. The isolated A subunit of the toxin claim 2.

5. The isolated B subunit of the toxin claim 2.

6. The isolated toxin of claim 1 wherein the toxin is a recombinant toxin.

7. The isolated toxin of claim 6 wherein the toxicity is greater than $10^9$ $CD_{50}$ per mg toxin.

8. An isolated A subunit or fragment thereof of an $AB_5$ bacterial toxin, said A subunit having an amino acid sequence selected from the group consisting of:
   a) SEQ ID NO: 2,
   b) residues 22–347 of SEQ ID NO: 2,
   c) a sequence which shares at least 70% identity to [the sequence comprising] amino acids 22–347 of SEQ ID NO: 2,
   d) a fragment of the A subunit comprising at least 50 amino acids of SEQ ID NO: 2, the A subunit or fragment thereof having a subtilase domain.

9. The isolated A subunit or fragment thereof as in claim 8, wherein the fragment comprises at least 75 amino acids of SEQ ID NO: 2.

10. The isolated A subunit or fragment thereof as in claim 8, wherein the fragment comprises at least 100 amino acids of SEQ ID NO: 2.

11. The isolated A subunit or fragment thereof as in claim 8 comprising an amino acid sequence which shares at least 80% identity to the amino acid sequence of SEQ ID NO: 2.

12. The isolated A subunit or fragment thereof as in claim 8, wherein the toxin activity of the fragment is inhibited by reason of a mutation selected from the group consisting of a mutations in:
   a) the Asp catalytic domain,
   b) the His catalytic domain, and
   c) the Ser catalytic domain.

13. The isolated A subunit or fragment thereof as in claim 8, wherein the toxin activity of the fragment is inhibited by reason of a mutation selected from the group consisting of a mutations in:
   a) the Asp active site residue,
   b) the His active site residue, and
   c) the Ser active site residue.

14. The isolated A subunit or fragment thereof as in claim 13, wherein the toxin activity is inhibited by reason of a substitution mutation of the Ser active site residue.

15. The isolated A subunit or fragment thereof as in claim 12, wherein the inhibition of activity is at least 90%.

16. An isolated B subunit or fragment thereof of an $AB_5$ bacterial toxin, said B subunit having a sequence selected from the group consisting of:
   a) SEQ ID NO: 3,
   b) residues 24–141 of SEQ ID NO: 3, c) a sequence which shares at least 70% identity to the sequence comprising amino acids 24–141 of SEQ ID NO: 3, d) a fragment of the B subunit comprising at least 50 amino acids of SEQ ID NO: 3, the A subunit of the toxin having a subtilase domain, and the B subunit or fragment thereof having the ability to recognize cell surface oligosaccharide component GM2(GalNAcβ[1→4](NeuAcα[2→3]Galβ[1→4Glcβ-).

17. The isolated B subunit or fragment thereof as in claim 16, wherein the fragment comprises at least 75 amino acids of SEQ ID NO: 3.

18. The isolated B subunit or fragment thereof as in claim 16, wherein the fragment comprises at least 100 amino acids of SEQ ID NO: 3.

19. The isolated B subunit or fragment thereof as in claim 16 comprising an amino acid sequence which shares at least 80% identity to the amino acid sequence of SEQ ID NO: 3.

* * * * *